United States Patent
Zhang et al.

(10) Patent No.: US 11,931,572 B1
(45) Date of Patent: Mar. 19, 2024

(54) SYSTEM AND METHOD FOR PROVIDING TRANSCUTANEOUS OR SUBCUTANEOUS TEMPORAL INTERFERENCE SPINAL CORD STIMULATION

(71) Applicant: ADVANCED NEUROMODULATION SYSTEMS, INC., Plano, TX (US)

(72) Inventors: Simeng Zhang, Frisco, TX (US); Hyun-Joo Park, Frisco, TX (US); Erika Ross, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 489 days.

(21) Appl. No.: 17/133,985

(22) Filed: Dec. 24, 2020

(51) Int. Cl.
- *A61N 1/04* (2006.01)
- *A61N 1/06* (2006.01)
- *A61N 1/32* (2006.01)
- *A61N 1/36* (2006.01)

(52) U.S. Cl.
CPC ....... *A61N 1/36034* (2017.08); *A61N 1/0456* (2013.01); *A61N 1/0492* (2013.01); *A61N 1/06* (2013.01); *A61N 1/323* (2013.01)

(58) Field of Classification Search
CPC .............. A61N 1/36034; A61N 1/0456; A61N 1/0492; A61N 1/06; A61N 1/323; G06F 3/016; G06F 2203/04101; G06F 2203/04112; G06F 3/0412; G06F 3/04166; G06F 3/042; G06F 3/0443; G06F 3/0446; G06F 3/0448; G06F 3/047; A61B 17/135; A61B 5/026; A61B 8/06; G01C 19/66; G09G 5/18

See application file for complete search history.

(56) References Cited

U.S. PATENT DOCUMENTS

| | | | |
|---|---|---|---|
| 11,020,590 B2 | 6/2021 | Pakhomov et al. | |
| 2004/0059394 A1* | 3/2004 | Carroll | A61N 1/323 607/43 |
| 2017/0036029 A1* | 2/2017 | Carroll | A61N 1/0553 |
| 2020/0138313 A1 | 5/2020 | Clements et al. | |
| 2020/0360697 A1 | 11/2020 | Paoles et al. | |
| 2021/0267523 A1* | 9/2021 | Donoghue | A61N 1/0529 |
| 2021/0370063 A1 | 12/2021 | Abouelsoud | |

* cited by examiner

*Primary Examiner* — Carl H Layno
*Assistant Examiner* — Anh-Khoa N Dinh
(74) *Attorney, Agent, or Firm* — Norton Rose Fulbright US LLP

(57) ABSTRACT

A noninvasive/minimally invasive neuromodulation system and method for providing therapy to a target neural tissue of a patient. In one arrangement, an example method comprises applying at least two input waveforms to respective pairs of electrodes affixed on the patient's skin or subcutaneously disposed relative to the target neural tissue, wherein the frequencies of the input waveforms are configured such that they combine, when simultaneously applied, to generate a beat waveform having a beat frequency due to interference. The beat waveform is causative of a transcutaneous/subcutaneous temporal interference (T/STI) electric field generated in the patient body, the T/STI electric field including an interference region at least partially overlapping the target neural tissue of the patient, wherein the beat frequency is of a value operative to impart a therapeutic effect to the target neural tissue.

19 Claims, 12 Drawing Sheets

DETERMINING PLACEMENT OF THE AT LEAST TWO PAIRS DEPENDING ON INTERROGATING A TTI PATTERN DATABASE HAVING ONE OR MORE ESTIMATED TTI PATTERNS FOR DIFFERENT COMBINATIONS OF ELECTRODE PLACEMENT CONFIGURATIONS, NUMBER OF ELECTRODE PAIRS, A RANGE OF AMPLITUDES AND FREQUENCIES, WHEREIN AT LEAST ONE TTI PATTERN INCLUDES AN INTERFERENCE REGION SUBSTANTIALLY CORRESPONDING TO THE LOCATION OF THE TARGET NEURAL TISSUE OF THE PATIENT FOR A GIVEN RANGE OF PARAMETERS AND ELECTRODE CONFIGURATION — 510

MAINTAINING A FREQUENCY OF THE FIRST INPUT WAVEFORM AT A FIRST CONSTANT VALUE OVER A PERIOD OF TIME OF THERAPY — 522

MAINTAINING A FREQUENCY OF THE SECOND IINPUT WAVEFORM AT A SECOND CONSTANT VALUE OVER THE PERIOD OF TIME OF THERAPY — 524

MAINTAINING OR VARYING THE AMPLITUDES/FREQUENCIES OF THE FIRST AND SECOND INPUT WAVEFORMS OVER THE THERAPY PERIOD — 526

VARYING A FREQUENCY OF THE FIRST INPUT WAVEFORM TO INCLUDE REPEATING PATTERNS OF A FIRST PORTION OF A FIRST HIGH FREQUENCY AND A SECOND PORTION OF A FIRST LOW FREQUENCY OVER A PERIOD OF TIME OF THERAPY
— 532

VARYING A FREQUENCY OF THE SECOND INPUT WAVEFORM TO INCLUDE REPEATING PATTERNS OF A FIRST PORTION OF A SECOND HIGH FREQUENCY AND A SECOND PORTION OF A SECOND LOW FREQUENCY OVER THE PERIOD OF TIME OF THERAPY, WHEREIN THE BEAT WAVEFORM INCLUDES A REPEATING PATTERN OF A HIGH FREQUENCY PORTION AND A LOW FREQUENCY PORTION FOR EACH BEAT PERIOD OVER THE THERAPY PERIOD
— 534

VARYING AN AMPLITUDE (E.G., THE FIRST AMPLITUDE) OF THE FIRST INPUT WAVEFORM SUCH THAT THE FIRST PORTION COMPRISING THE FIRST HIGH FREQUENCY HAS A FIRST HIGH AMPLITUDE AND THE SECOND PORTION COMPRISING THE FIRST LOW FREQUENCY HAS A FIRST LOW AMPLITUDE
— 542

VARYING AN AMPLITUDE (E.G., THE SECOND AMPLITUDE) OF THE SECOND INPUT WAVEFORM SUCH THAT THE FIRST PORTION COMPRISING THE SECOND HIGH FREQUENCY HAS A SECOND HIGH AMPLITUDE AND THE SECOND PORTION COMPRISING THE SECOND LOW FREQUENCY HAS A SECOND LOW AMPLITUDE, THEREBY CAUSING THE HIGH FREQUENCY PORTION OF THE BEAT WAVEFORM TO HAVE A HIGHER AMPLITUDE DETERMINED AS A FUNCTION OF THE FIRST AND SECOND HIGH AMPLITUDES
— 544

SYSTEM AND METHOD FOR PROVIDING TRANSCUTANEOUS OR SUBCUTANEOUS TEMPORAL INTERFERENCE SPINAL CORD STIMULATION

TECHNICAL FIELD

The present disclosure generally relates to neuromodulation. More particularly, and not by way of any limitation, the present disclosure is directed to a system and method for providing transcutaneous or minimally invasive temporal interference spinal cord stimulation.

BACKGROUND

Implantable medical devices (IMDs) have changed how medical care is provided to patients having a variety of chronic illnesses and disorders, wherein a treatment may be based on neurostimulation for certain therapy applications. Respective types of implantable neurostimulators or pulse generators (IPGs) may be configured to provide a reduction in pain for chronic pain patients and reduce motor difficulties in patients with Parkinson's disease and other movement disorders. For example, spinal cord stimulation (SCS) involves applying an electrical current into particular regions of the spinal cord using implantable electrodes to induce paresthesia, which is a subjective sensation of numbness or tingling in a region of the body associated with the stimulated spinal cord region. Paresthesia masks the transmission of chronic pain sensations from the afflicted regions of the body to the brain, thereby providing pain relief to the patient. Typically, an SCS system delivers electrical current through electrodes implanted on top of the dura layer surrounding the spinal cord. The electrodes may be carried, for example, by a paddle lead, which has a paddle-like configuration with the electrodes arranged in one or more independent columns on a relatively large surface area, or via a percutaneous lead, which includes the electrodes arranged around a tube. Conventional delivery of implantable electrode leads for SCS generally requires invasive surgical procedures involving incisions and/or substantial removal of lamina, resulting in trauma to the patient and longer procedure time. Similar challenges and disadvantages apply to other forms of leads implanted to treat other medical conditions through electrical stimulation. For example, implantable devices for deep brain stimulation (DBS), cardiac rhythm management (CRM), occipital nerve stimulation (ONS), peripheral nerve stimulation (PNS), motor cortex stimulation (MCS), vagus nerve stimulation (VNS), and the like are often plagued by such challenges and disadvantages.

Noninvasive stimulation is known to be safer and more tolerable than invasive strategies. Accordingly, there is a resurgence of interest in noninvasive techniques for providing therapy. Whereas advances in noninvasive stimulation techniques such as transcranial direct current stimulation (tDCS), transcranial alternating-current stimulation (tACS), transcutaneous electrical nerve stimulation (TENS), etc., continue to take place, several lacunae remain, thereby requiring further innovation as will be set forth hereinbelow.

SUMMARY

Example embodiments of the present patent disclosure are directed to a noninvasive or minimally invasive (e.g., subcutaneous) neuromodulation system and method for providing therapy to a target neural tissue of a patient based on a temporal interference phenomenon caused by two or more input waveforms generated using a related number of electrodes that may be placed on a patient's skin or disposed minimally invasively (e.g., subcutaneous placement). A beat waveform caused by the temporal interference may be configured to be localized to a target tissue area based on waveform engineering techniques set forth herein. Depending on whether transcutaneous electrodes and/or minimally invasive electrodes (e.g., subcutaneous electrodes placed under a patient's skin) are used in an example implementation, the temporal inference phenomenon causing the beat waveforms according to the teachings herein may be referred to as transcutaneous temporal interference (TTI) or subcutaneous temporal interference (STI), which may collectively be referred to as cumulative focal stimulation or CFS in some example embodiments. Accordingly, unless otherwise specifically stated, the terms "transcutaneous temporal interference", "subcutaneous temporal interference", "temporal interference" and "cumulative focal stimulation", as well as corresponding acronyms, abbreviations, or initialisms, i.e., "TTI", "STI", "TI" and "CFS", are used somewhat roughly analogously and/or interchangeably for purposes of the present patent disclosure. In similar fashion, the terms "noninvasive" and "minimally invasive" are also somewhat roughly analogously and/or interchangeably used in some example embodiments of the present patent disclosure, and may be comprehended under the term "noninvasive/minimally invasive" or "NIMI" for purposes herein.

In one arrangement, an example method comprises applying at least two input waveforms to respective pairs of electrodes affixed on the patient's skin or minimally invasively disposed at respective locations relative to the target neural tissue, wherein respective frequencies of the input waveforms may be configured such that they combine, when simultaneously applied, to generate a modulated waveform, referred to herein as a beat waveform, having a beat frequency due to interference. The beat waveform is causative of and/or comprises a transcutaneous (or subcutaneous) temporal interference (T/STI) electric field generated in the patient body. Depending on waveform engineering in one implementation, the T/STI field may be controlled to include an interference region at least partially overlapping the target neural tissue of the patient, wherein the beat frequency is of a value operative to impart a therapeutic effect to the target neural tissue.

In one aspect, an embodiment of a noninvasive/minimally invasive (NIMI) neuromodulator for providing therapy to a target neural tissue of a patient is disclosed. Example NIMI neuromodulator may comprise, inter alia, at least a first input source operative to generate a first input waveform and at least a second input source operative to generate a second input waveform. In one arrangement, the first and second input waveforms may comprise sinusoid current signals, wherein the first input waveform is configured with a first amplitude and a first frequency and the second input waveform is configured with a second amplitude and a second frequency. Example neuromodulator may include a first and a second pair of electrodes attachable at respective locations relative to the target neural tissue of the patient. A controller configured to control the first and second input sources may included, which may be operative responsive to a set of program instructions executing to perform following: applying the first input waveform to the first pair of the electrodes, the first input waveform having the first amplitude and the first frequency; and applying the second input waveform to the second pair of the electrodes, the second input waveform having the second amplitude and the second frequency, wherein the second frequency is configured to be different from the first frequency such that the first and second input waveforms combine, when substantially simultaneously applied, to generate a beat waveform having a beat frequency due to interference, the beat waveform causing a CFS electric field (i.e., a T/STI field) having an interference region at least partially overlapping the target neural tissue of the patient, wherein the beat frequency (i.e., the number of beats per second) is of a value operative to impart a therapeutic effect to the target neural tissue.

In one arrangement, a controller of the NIMI neuromodulator may be further configured to perform maintaining the first frequency of the first input waveform at a first constant value over a therapy period, and maintaining the second frequency of the second input waveform at a second constant value over the therapy period such that nonvarying beats may be generated in the CFS field.

In another arrangement, a controller of the NIMI neuromodulator may be further configured to perform varying the first frequency of the first input waveform to include repeating patterns of a first portion of a first high frequency and a second portion of a first low frequency over a therapy period, and varying the second frequency of the second input waveform to include repeating patterns of a first portion of a second high frequency and a second portion of a second low frequency over the therapy period, wherein the modulated beat waveform includes a corresponding repeating pattern of a high frequency portion and a low frequency portion for each beat period over the therapy period. In a still further arrangement, the controller may be configured to vary the first amplitude of the first input waveform such that the first portion comprising the first high frequency has a first high amplitude and the second portion comprising the first low frequency has a first low amplitude. The controller may also be configured to vary the second amplitude of the second input waveform such that the first portion comprising the second high frequency has a second high amplitude and the second portion comprising the second low frequency has a second low amplitude, thereby causing the high frequency portion of the beat waveform to have a higher amplitude determined as a function of the first and second high amplitudes, which in some embodiments is functionally similar to burst stimulation generated using an IPG device.

In another aspect, an embodiment of a NIMI neuromodulation method for providing therapy to a target neural tissue of a patient is disclosed. Example method may comprise, inter alia, affixing at least two pairs of electrodes on the patient's skin or subcutaneously at respective locations relative to the target neural tissue; applying a first input waveform having a first amplitude and a first frequency to a first pair of the at least two pairs of electrodes; and applying a second input waveform having a second amplitude and a second frequency to a second pair of the at least two pairs of electrodes, the second frequency configured to be different from the first frequency such that the first and second input waveforms combine, when substantially simultaneously applied, to generate a beat waveform having a beat frequency due to interference, the beat waveform causing a T/STI electric field having an interference region at least partially overlapping the target neural tissue of the patient, wherein the beat frequency is of a value operative to impart a therapeutic effect to the target neural tissue. In one arrangement, example NIMI neuromodulation method may comprise determining placement of the at least two pairs of electrodes based on interrogating a T/STI pattern database having a plurality of T/STI patterns (i.e., TI or CFS patterns) for different combinations involving, e.g., electrode placement configurations, number of electrode pairs, a range of amplitudes corresponding respectively to the first and second input waveforms, and a range of frequencies corresponding respectively to the first and second input waveforms. In one arrangement, the T/STI patterns may be developed, estimated, extrapolated, or otherwise obtained based on computational modeling techniques such as, e.g., finite element modeling, involving human and/or animal models. In one arrangement, an example NIMI neuromodulation method may involve maintaining constant parametrics of the first and/or second input waveforms over a therapy period. In another embodiment, an example NIMI neuromodulation method may involve introducing temporal dynamics into either of the first and second amplitudes of the first and second input waveforms, and/or either of the first and second frequencies of the first and second input waveforms in order to generate complex T/STI waveforms that may mimic IPG-based burst stimulation in some scenarios. In a still further arrangement, constant parametrics-based therapy portions may be interspersed with variable parametrics-based therapy portions in a configurable manner.

In still further aspects, an apparatus and associated non-transitory computer-readable medium or media containing computer-executable program instructions or code portions stored thereon are disclosed for performing example methods herein when executed by a processor entity of the apparatus including a NIMI neuromodulator. Example apparatus or equipment may be deployed as a patient controller device, a clinician programmer device, a delegated agent device, etc., either in standalone and/or networked mode in some embodiments, that may be configured appropriately, mutatis mutandis, to generate and apply at least two input waveforms that can combine to form a T/STI electric field with an interference region overlapping a target tissue site in a patient.

In a still further embodiment, one or more implanted electrodes may be used in combination with a NIMI electrode arrangement, wherein a T/STI field may include or combine the electric fields generated by the implanted electrodes as well as the fields generated by the external/NIMI electrodes. In a still further embodiment, a T/STI scheme may be used (e.g., in combination with specific temporal and/or amplitude patterns) in an arrangement such that the T/STI scheme is utilized as a NIMI "predictor" of a potential invasive SCS therapy, e.g., as a noninvasive trial period precursor, to assess how different stimulations may impact the patient. In some therapy settings, it may be preferable to have an initial phase of a noninvasive T/STI scheme (e.g., for a select time duration) followed by IPG-based therapy, whereby power consumption for the T/STI scheme may be minimized.

Additional/alternative features and variations of the embodiments as well as the advantages thereof will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 5A-5F depict flowcharts illustrative of blocks, steps and/or acts that may be (re)combined in one or more arrangements with or without additional flowcharts of the present patent disclosure for facilitating T/STI-based NIMI neuromodulation according to some embodiments of the present patent disclosure;

DETAILED DESCRIPTION

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like set forth in reference to other embodiments herein. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some example embodiments described herein may relate to a noninvasive neuromodulator system for providing therapy to a desired area of a body or tissue based on a suitable stimulation therapy application, such as a spinal cord stimulation (SCS) system. However, it should be understood that example embodiments disclosed herein are not limited thereto, but have broad applicability, including but not limited to a variety of therapy applications involving different types of target tissues and organ systems such as neuromuscular systems, dorsal root ganglia (DRG), deep brain tissue, gastrointestinal system, etc.

Figure 1A:
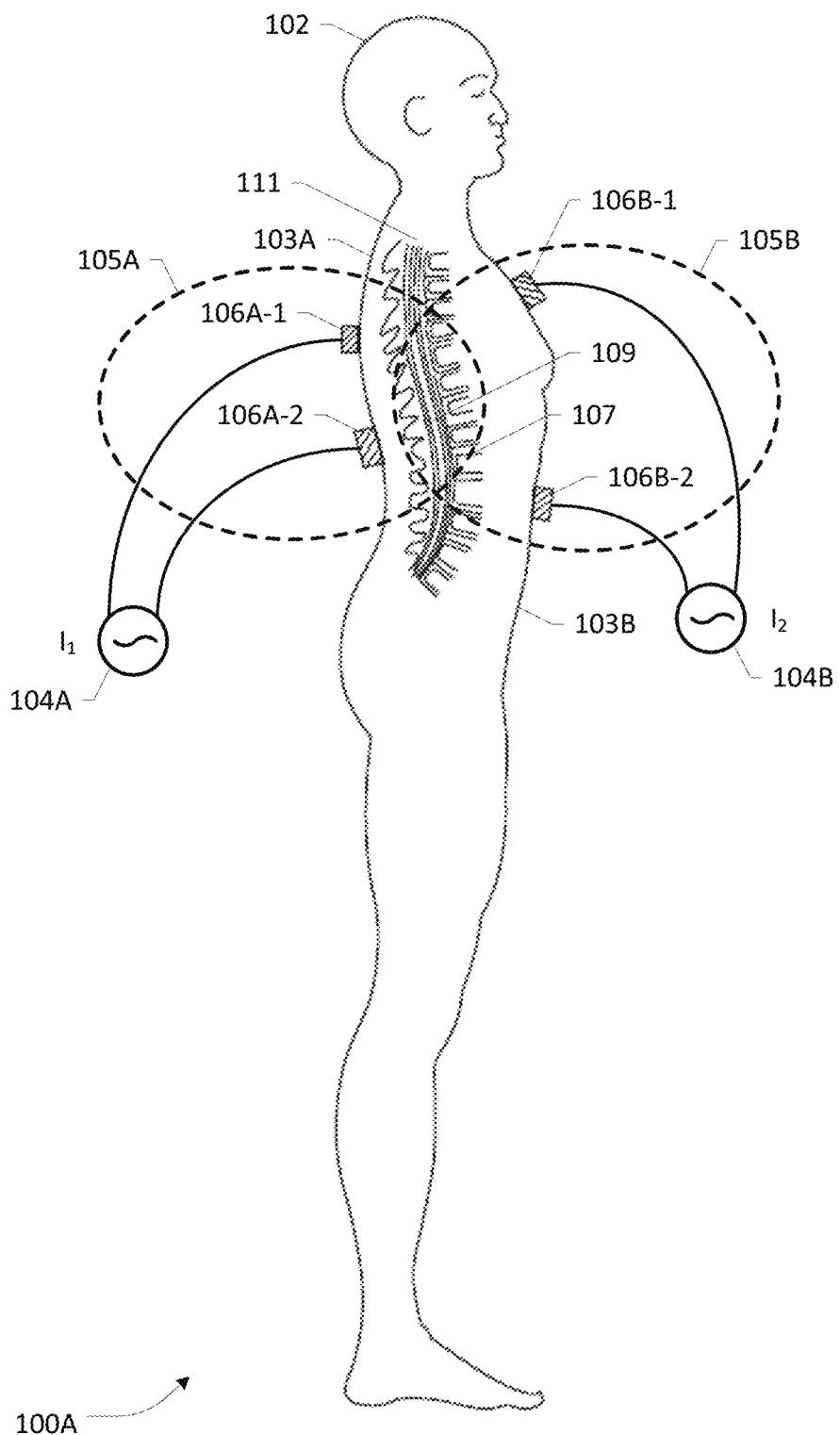
FIG. 1A depicts an example NIMI neuromodulation system for providing therapy by effectuating transcutaneous/subcutaneous temporal interference (T/STI) at a target neural tissue according to an embodiment of the present patent disclosure.

Referring to FIG. 1A, depicted therein is an example NIMI neuromodulation system for providing therapy at a target neural tissue of a patient according to an embodiment of the present patent disclosure. Example system 100A may include two or more input waveform sources 104A, 104B, each operative to energize a corresponding pair of electrodes 106A-1, 106A-2 and 106B-1, 106B-2, respectively, that may be placed, attached or otherwise affixed externally on the skin of a patient 102, or disposed subcutaneously, proximate to a target neural tissue of the patient 102. In general operation, each source 104A, 104B may be activated to generate respective waveforms having certain characteristics (e.g., the amplitudes, frequencies, respective temporal variations therein over a period of time, etc.) that can be selectively configured such that when the waveforms are applied to the corresponding electrodes, they each generate an oscillating electric field propagating into the patient's body transcutaneously/subcutaneously. The source waveform characteristics may be tuned or otherwise calibrated such that the resulting oscillating electric fields may be controlled to interact with each other in the patient body in an interferential manner at a particular site, referred to herein as transcutaneous or subcutaneous temporal interference (T/STI), depending on the electrode placement, in order to generate a modulated field having an interference region with a "beat" frequency that is in a range known to cause therapeutic effects in neural tissue. As will be seen further below in detail, various electrode placement configurations relative to the location of a target tissue, the number of input waveforms and associated electrode pairs as well as the parametrics of the source waveforms as such as, e.g., amplitudes, frequencies, etc., may be varied and combined in myriad arrangements to achieve different T/STI patterns such that the resulting modulated fields can be steered to specific target neural tissues of a patient according to the teachings herein.

In one arrangement, temporal interference may be achieved by simulataneously applying two (or more) electric waveforms (e.g., sinusoids), both at a high but slightly different frequencies via two (or more) pairs of electrodes activated by suitable sources (e.g., current sources). The summation of two high frequency (HF) sine waves of slightly different frequencies results in a waveform that is a HF carrier-wave (i.e., average of the two sine waves) modulated by a low frequency envelope oscillating at a "beat" frequency. This beat frequency is the difference of the frequencies of the two input sinusoids. Whereas neurons do not get activated by high frequencies (e.g., >around 500 Hz) due to their intrinsic low-pass filtering, example embodiments herein may be configured to generate modulated electric fields having envelopes with beat frequencies less than 100 Hz at specific target sites, thereby advantageously leading to stimulation and/or neuromodulation.

Exemplary neuromodulation system 100A of FIG. 1A is illustrated with two input waveform sources, represented by a first current source 104A operative to generate a first current signal $I_1$ (e.g., an oscillating or alternating current AC) signal) and a second current source 104B operative to generate a second current signal $I_2$ (e.g., an oscillating or alternating current (AC) signal). Input sources 104A, 104B may be activated simultaneously to apply the currents to specific locations on the patient's body via electrically isolated pairs of electrodes, 106A-1, 106A-2 and 106B-1, 106B-2, respectively. The currents may comprise sinusoid waves having frequencies $f_1$ and $f_2$, respectively, which may be higher than the range of frequencies of normal neural operation but with a small difference $\Delta f = |f_1 - f_2|$ that is within the range of frequencies of normal neural operation. In one example arrangement, the applied frequencies $f_1$ and $f_2$ may be in the kilohertz (kHz) range and the currents may be in the range of a few mA or a fraction thereof to one or more Amperes, although different frequency and current magnitudes may be applied in an example embodiment depending on the patient, selected target tissue for therapy, location of the electrodes, etc. Further, electrode pairs 106A-1, 106A-2 and 106B-1, 106B-2 may be placed at respective locations on the patient's body, which may be based on the physician's knowledge of the intended target neural tissue, e.g., a specific location of or relative to the patient's spinal cord 111, as well as the type of therapy being applied. By way of illustration, electrode pair 106A-1, 106A-2 may be affixed on a dorsal surface 103A of the patient 102, e.g., the lower, upper, or middle of the back and/or on either lateral/medial side of the vertebral column, whereas electrode pair 106B-1, 106B-2 may be affixed on a ventral surface 103B of the patient 102, e.g., the chest and/or abdomen and/or on either side of the sagittal plane of the patient's body. Applied currents $I_1$ and $I_2$ are operative to create respective electric fields 105A, 105B, that propagate three-dimensionally inside the patient's body, wherein respective electric fields 105A, 105B interact via superposition, thereby creating a superposition field 107 having a volume that at least partially encompasses or overlaps the intended target neural tissue, e.g., dorsal column 109. As set forth further below, superposition field 107, also referred to as interference field or region, comprises an oscillating field having an envelope amplitude that is modulated periodically at a frequency equal to the difference frequency $\Delta f$, sufficiently low to drive, suppress or otherwise modulate neural activity of the target tissue. It will be recognized upon reference hereto that the peak amplitude of the envelope modulation of an interference region can be steered and/or focused in depth depending on the various electrical characteristics of the applied current waveforms as well as the number of electrode pairs and their respective placement in order to take into account and/or compensate for any anatomical barriers that may be present with respect to certain target neural tissues of a patient.

The foregoing principles may be formalized as follows with two example sinusoid signal waveforms, $S_1$, $S_2$, having normalized amplitudes, represented as:

$$S_1 = \sin(2\pi f_1 t) \qquad \text{Eqn. (1)}$$

$$S_2 = \sin(2\pi f_2 t) \qquad \text{Eqn. (2)}$$

where the frequencies of each wave are $f_1$ and $f_2$, respectively, and t is the time.

The superposition of the two input waves is given by:

$$S_{1+2} = S_1 + S_2 = \sin(2\pi f_1 t) + \sin(2\pi f_2 t) \qquad \text{Eqn. (3)}$$

The foregoing expression may be written in a product term as:

$$S_{+2} = 2\sin(\pi(f_1+f_2)*t)*\cos(\pi(f_1-f_2)*t) \qquad \text{Eqn. (4)}$$

Eqn. (4) shows that $S_{1+2}$ is equivalent to a waveform having an amplitude twice as much as the $S_1$, $S_2$ waves, with a frequency of the average of $f_1$ and $f_2$ multiplied by another term with a frequency of half of the difference of $f_1$ and $f_2$. This multiplicative term is responsible for the beating effect, whose envelope can be extracted, wherein the beat frequency is given as $|f_1-f_2|$. As will be shown further below, frequency variations, amplitude variations, or both, may be introduced in the input sinusoids, thereby giving rise to more complex T/STI waveforms in some example embodiments. Furthermore, skilled artisans will recognize that due to the duality relationship between voltage and current signals, and associated correspondence with the electric fields caused thereby, example input waveforms set forth herein may be broadly conceptualized as representative of input currents, voltages and/or fields (i.e., collectively referred to as sources), with the concomitant interference waveforms being representative of voltages, currents and/or fields caused by the respective input waveforms. It will be further realized that the foregoing T/STI principles are also equally applicable to more than two input waveform sources, mutatis mutandis, wherein a resultant field waveform is a superposition of and caused by all input waveforms, wherein an interference region may be determined or controlled by appropriately calibrating the number and/or electrical parameters of respective input sources, electrode placement, etc., generally referred to herein as "waveform engineering".

In another arrangement, system 100A may also optionally include an implantable pulse generator (IPG) having a lead system with one or more implanted electrodes (not specifically shown in this FIG.), which may be stimulated in a manner so as to cause another electric field operative to be included in the T/STI envelope, e.g., superposition region 107, with respect to specific structural components associated with the intended target tissue 109. It will be recognized such an IPG-based electric field modulation scheme may be configured to provide fine-tuning of a T/STI and may comprise a further variation of waveform engineering for purposes of some embodiments herein. Additional details relating to IPGs and related lead systems, which may be used in conjunction with a NIMI neuromodulation system of the present patent disclosure, may be found in, e.g., (i) U.S. Pat. No. 10,207,103, entitled "IMPLANTABLE THIN FILM DEVICES"; (ii) U.S. Pat. No. 7,571,007, entitled "SYSTEMS AND METHODS FOR USE IN PULSE GENERATION", and (iii) U.S. Patent Application Publication No. 2014/0343564, entitled "PADDLE LEADS FOR NEUROSTIMULATION AND METHOD OF DELIVERING THE SAME", each of which is incorporated herein by reference.

Figure 1B:
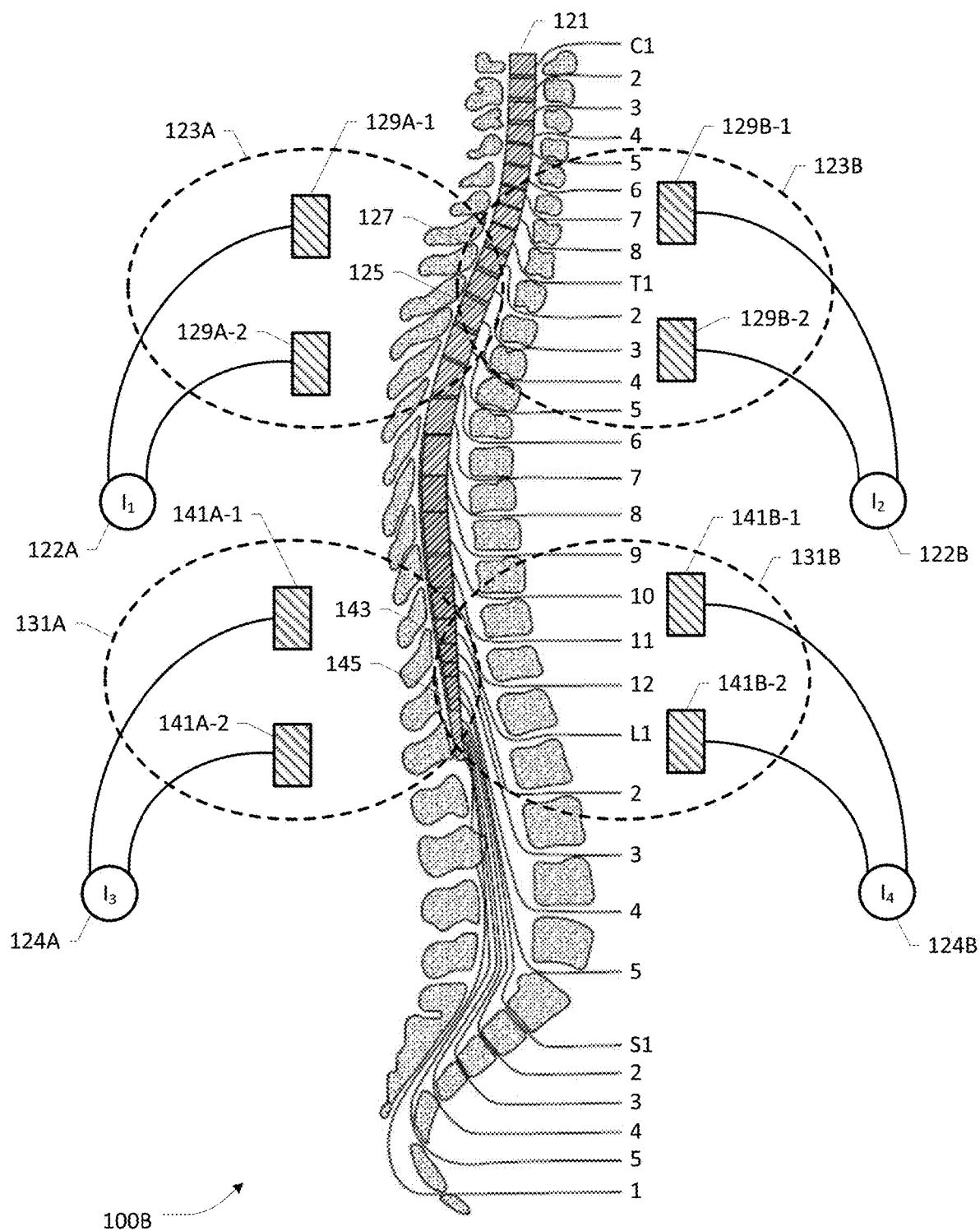
FIG. 1B depicts another example NIMI neuromodulation system for providing T/STI-based therapy according to an embodiment of the present patent disclosure.

FIG. 1B depicts another example NIMI neuromodulation system according to an embodiment of the present patent disclosure wherein different spinal cord regions and/or nerves may be individually targeted for providing TTI-based therapy with respect to different regions of a patient's body. As illustrated, example system 100B includes two pairs of input sources 122A/122B and 124A/124B for energizing respective pairs of electrodes that may be placed at different locations relative to the patient's spinal cord 121 (e.g., transcutaneously and/or subcutaneously). As is known, spinal nervous tissue includes "spinal nerve roots," which comprise the 31 pairs of nerves that emerge from the spinal cord. Spinal nerve roots may be cervical nerve roots, thoracic nerve roots, and lumbar nerve roots. Each exterior region, or each dermatome, of the human body is associated with a particular spinal nerve root at a particular longitudinal spinal position. For example, the head and neck regions are associated with C2-C8, the back regions extend from C2-S3, the central diaphragm is associated with spinal nerve roots between C3 and C5, the upper extremities correspond to C5 and T1, the thoracic wall extends from T1 to T11, the peripheral diaphragm is between T6 and T11, the abdominal wall is associated with T6-L1, lower extremities are located from L2 to S2, and the perineum from L4 to S4. Accordingly, when a patient experiences pain in one of these regions, electrode pairs may be externally attached to the patient's body adjacent/proximate to the spinal cord at the corresponding spinal position for providing NIMI therapy by steering a TTI field thereto according to some embodiments herein. For example, to address chronic pain sensations that commonly focus on the lower back and lower extremities, two or more pairs of electrodes may be placed on the patient's body such that when the electrodes are energized appropriately, they generate a TTI field directed to the spinal column portion between vertebrae levels T8 and T12 that is operative to cause amelioration or palliation of the pain sensation.

By way of illustration, therapy system 100B in FIG. 1B is exemplified with a first pair of input current sources 122A/122B operative to energize electrode pairs 129A-1, 129A-2 and 129B-1, 129B-2, for causing respective electric fields 123A, 123B, which can be modulated to have a superposition region 127 overlapping any of the spinal nervous tissue associated with lower cervical roots and/or upper thoracic roots, e.g., representatively shown as nervous tissue 125. Likewise, a second pair of input current sources 124A/124B are operative to energize electrode pairs 141A-1, 141A-2 and 141B-1, 141B-2, for causing respective electric fields 131A, 131B, which can be modulated to have a superposition region 143 overlapping any of the spinal nervous tissue associated with lower thoracic roots and/or upper lumbar roots, e.g., representatively shown as nervous tissue 145.

Skilled artisans will recognize that the placement of electrode pairs 129A-1, 129A-2 and 129B-1, 129B-2, and electrode pairs 141A-1, 141A-2 and 141B-1, 141B-2 may be varied in numerous combinations relative to the directionality and/or anatomical planes and axes associated with a patient (e.g., caudal/rostral, dorsal/ventral, medial/lateral, etc.), wherein any of the electrodes or electrode pairs may be placed on the back, on the front, and/or on the side(s) of the patient. Further, although input current sources 122A/122B and 122A/122B are illustrated in FIG. 1B as four separate entities, they may be integrated in a single neuromodulator device or apparatus having a multi-channel output, wherein each channel may be configured to drive a corresponding electrode pair, respectively.

Figure 1C:
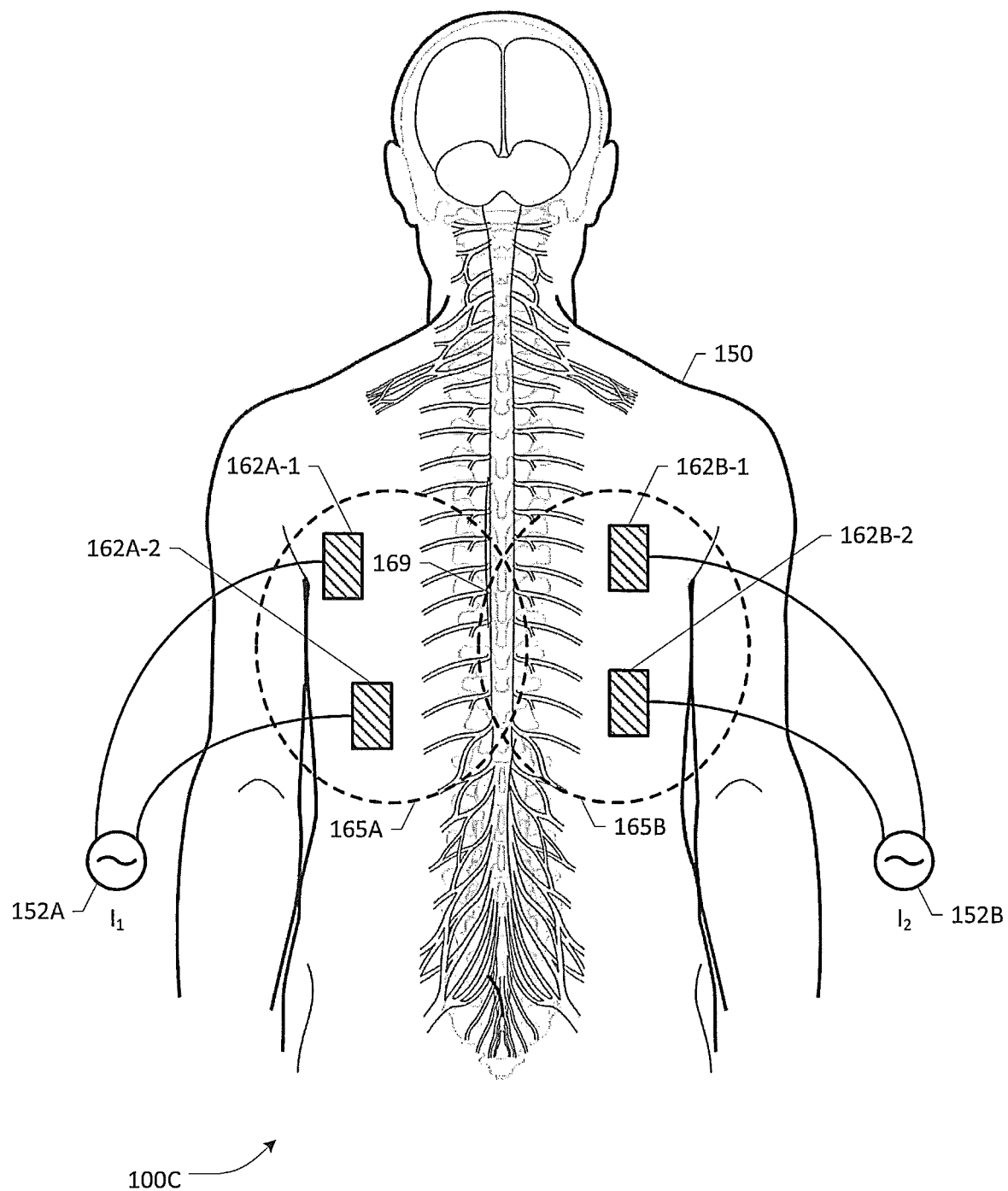
FIG. 1C depicts another example NIMI neuromodulation system for providing T/STI-based therapy according to an embodiment of the present patent disclosure.

FIG. 1C depicts another example NIMI neuromodulation system 100C for providing TTI-based therapy according to an embodiment of the present patent disclosure, wherein example NIMI electrodes are placed on a patient's back or subcutaneously that are laterally spaced from the patient's spinal column. As illustrated, input waveform sources 152A and 152B are operative to energize respective electrode pairs 162A-1, 162A-2 and 162B-1, 162B-2, which may be placed at suitable locations on/in the dorsal anatomy of patient 150. Similar to the embodiments set forth above, electrode pairs 162A-1, 162A-2 and 162B-1, 162B-2 and corresponding input sources 152A, 152B may be configured to generate respective electric fields 165A, 165B, that may yield a superposition region 169 proximate to the intended spinal nervous tissue location.

Figure 2:
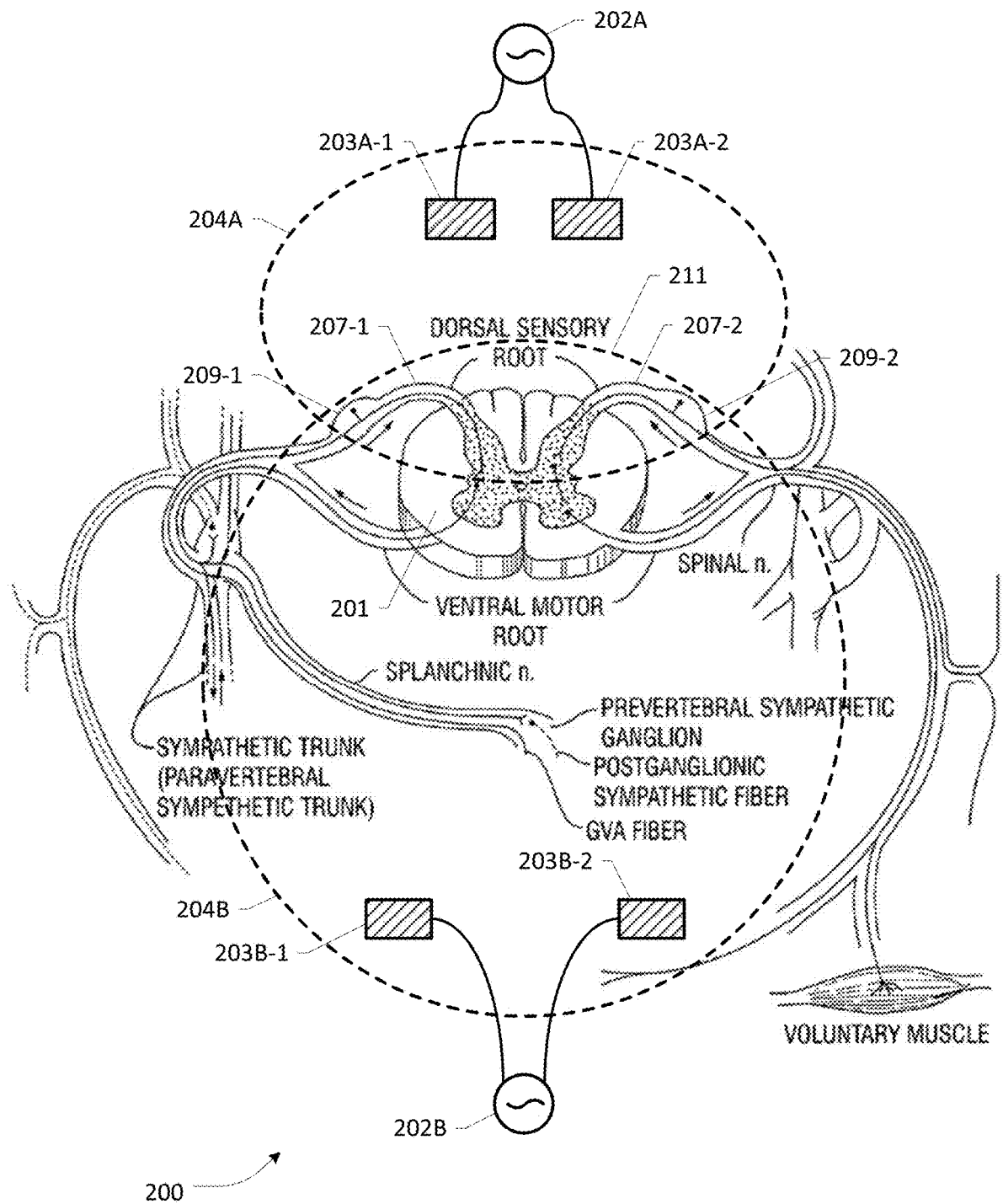
FIG. 2 depicts a cross-sectional view of a spinal cord illustrating additional features of a target neural tissue that may be stimulated based on T/STI according an embodiment of the present patent disclosure.

FIG. 2 depicts another neuromodulation system 200 wherein a cross-sectional view of a spinal cord 201 is illustrated with additional features relating to or of a target neural tissue that may be stimulated based on TTI according an embodiment of the present patent disclosure. Example neuromodulation system 200 may include two waveform sources 202A and 202B that may be configured to generate waveforms operative to effectuate electric fields having different propagation volumes, respectively, so as to facilitate stimulation of neural tissue at different depths in a patient's body. In one arrangement, electrodes 203A-1, 203A-2 may be placed on a patient's dorsal/posterior side (e.g., the back), and/or subcutaneously thereat, whereas electrodes 203B-1 and 203B-2 may be placed on the patient's ventral/anterior side (e.g., the chest and/or abdomen), and/or subcutaneously thereat, each electrode pair configured to be energized by the respective current waveform source 202A/202B. The waveforms generated by sources 202A and 202B may be controlled such that respective electric fields 204A, 204B may have different strengths (e.g., measured in Volts/meter) and/or wavefronts so as to cause an interference region 211 closer to the patient's back for targeting specific dorsal sensory root(s) 207-1/207-2 and/or associated dorsal root ganglia 209-1/209-2. In similar fashion, other neural tissue associated with a spinal cord, e.g., ventral motor roots, may also be stimulated by using appropriate waveform engineering techniques according to some embodiments herein.

In general, various parameters associated with the input waveforms of a neuromodulation system may be manipulated or modified in order to vary the shape of a resulting activation region caused by the T/STI of the waveforms, e.g., via waveform engineering, as previously noted. In one arrangement, the number of input fields or current sources (and corresponding electrode pairs) may be varied depending on the intended target tissue region to be stimulated, activated or other affected as part of therapy. In an example implementation, a two-pair arrangement may be deployed as shown in FIGS. 1A and 1C above, although more pairs can be added to more precisely steer the activation region in some embodiments. Independently or otherwise, the location of input fields (i.e., the electrodes) may also be varied depending on the therapy application being considered. For example, if a therapy application is configured with using two pairs of electrodes, a first pair can be located lateral to the spinal cord (e.g., on the patient's back) along the rostral-caudal direction of the patient's body, and a second pair can be located at the other side of the spinal cord, as exemplified in FIG. 1C. Such an arrangement may cause more superficial activation (e.g., for activating the dorsal column). Further, the distance of the electrode pairs to the spinal cord can be adjusted (e.g., in a lateral/medial direction) to change the width of the interference region, while the electrodes may also be moved along the spinal cord (e.g., in a rostral/caudal direction) to selectively activate longer or shorter sections of the spinal cord. In another example embodiment involving two electrode pairs, a first pair can be located across the chest with one electrode on the back, one electrode on the side rib cage (or the front chest) of the patient, and the other pair on the opposite side of the patient (e.g. in a mirror image placement relative to the placement of the first pair). This arrangement may result in a deeper activation, which can be used if the dorsal placement scheme set forth above is not able to activate the intended structures that are deep enough. Accordingly, an example across-body electrode placement may be configured to target deeper structures such as the dorsal root ganglion similar to the arrangement shown in FIG. 2 set forth above.

In a further variation, the strength of individual input fields/electrodes may be varied as well. Also, yet another independent variation may involve additional hardware such as nerve cuff electrodes that may be added to further assist in steering and shaping of the TTI activation region in a patient as a further refinement in field waveform engineering.

In still further embodiments, various parameters of input fields/sources can be independently, selectively, and/or optionally modified. In one example configuration, such parameters may be modified to vary the temporally interfered beat frequency of the T/STI field. For example, the input frequency of the source fields/currents may be varied or tuned such that various beat frequencies (which is the difference between the two (or more) frequencies of the input waveforms) that are better optimized for certain types of nerve tissue may be obtained. Additionally, the input frequencies do not have to be confined to a single frequency during the course of a therapy session, as will be described in additional detail further below. In a still further independent variation involving the strength of the individual input fields/sources, e.g., respective amplitudes/magnitudes, the resulting envelope's peak amplitude may be given as the sum of the two (or more) input amplitudes (which may be roughly correlated with a physical location coinciding with the middle or the centroid of electrode pairs' respective locations).

Figure 3:
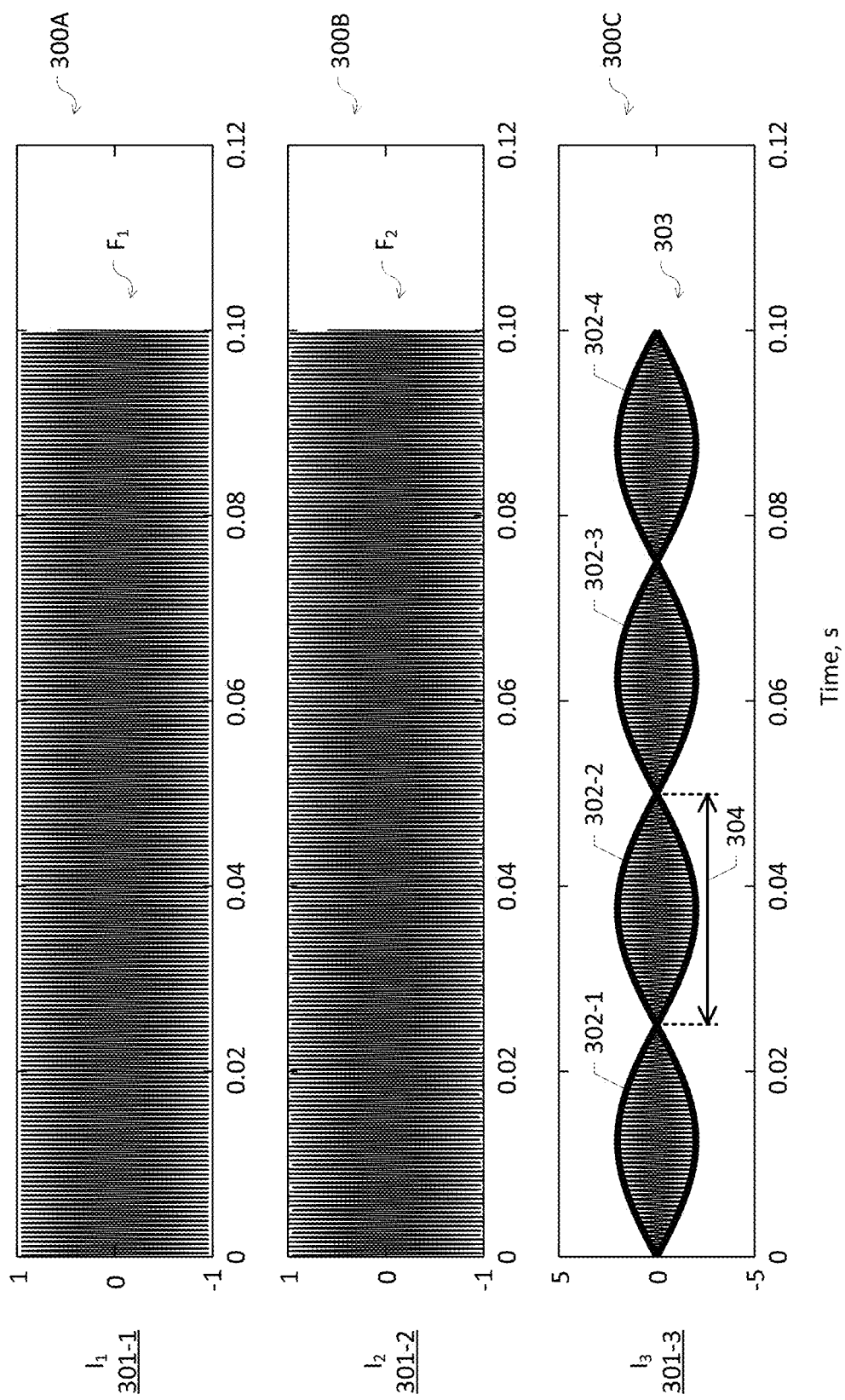
FIG. 3 depicts a panel of example input waveforms and resultant interference waveform for application in a T/STI-based therapy system according to an embodiment of the present patent disclosure.

FIG. 3 depicts a panel of example input source waveforms and resulting interference waveform for application in a CFS-based therapy system according to an embodiment of the present patent disclosure. Panels 300A, 300B depict two input source waveforms corresponding to two current signals, $I_1$ 301-1 and $I_2$ 301-2, having normalized amplitudes (i.e., each first and second amplitudes varying between −1 and +1) and respective frequencies, $f_1$ and $f_2$, that are relatively close to each other. For example, a first frequency of $f_1$=2000 Hz and a second frequency of $f_2$=2040 Hz may be applied in the illustrated embodiment, thereby giving rise to a resulting interference signal, e.g., $I_3$ 301-3, with an envelope 303 that has an amplitude twice as much as the amplitudes of $I_1$ 301-1 and $I_2$ 301-2, and a beat frequency $\Delta f=|f_1-f_2|=40$ Hz, which is within the range of frequencies operative of neural recruitment. Given that the beat frequency is 40 Hz, i.e., beats per second, four repeating beats 302-1 to 302-4 are exemplified in panel 300C for a total of 0.1 second, with each beat period comprising 0.025 second. As previously noted, in view of the duality and correspondence between the relevant electrical quantities, input waveforms 301-1 and 301-2 may be treated as being representative of input fields and resultant interference signal 301-3 may be treated as representative of the T/STI field caused thereby for purposes of some embodiments of the present patent disclosure.

Figure 4A:
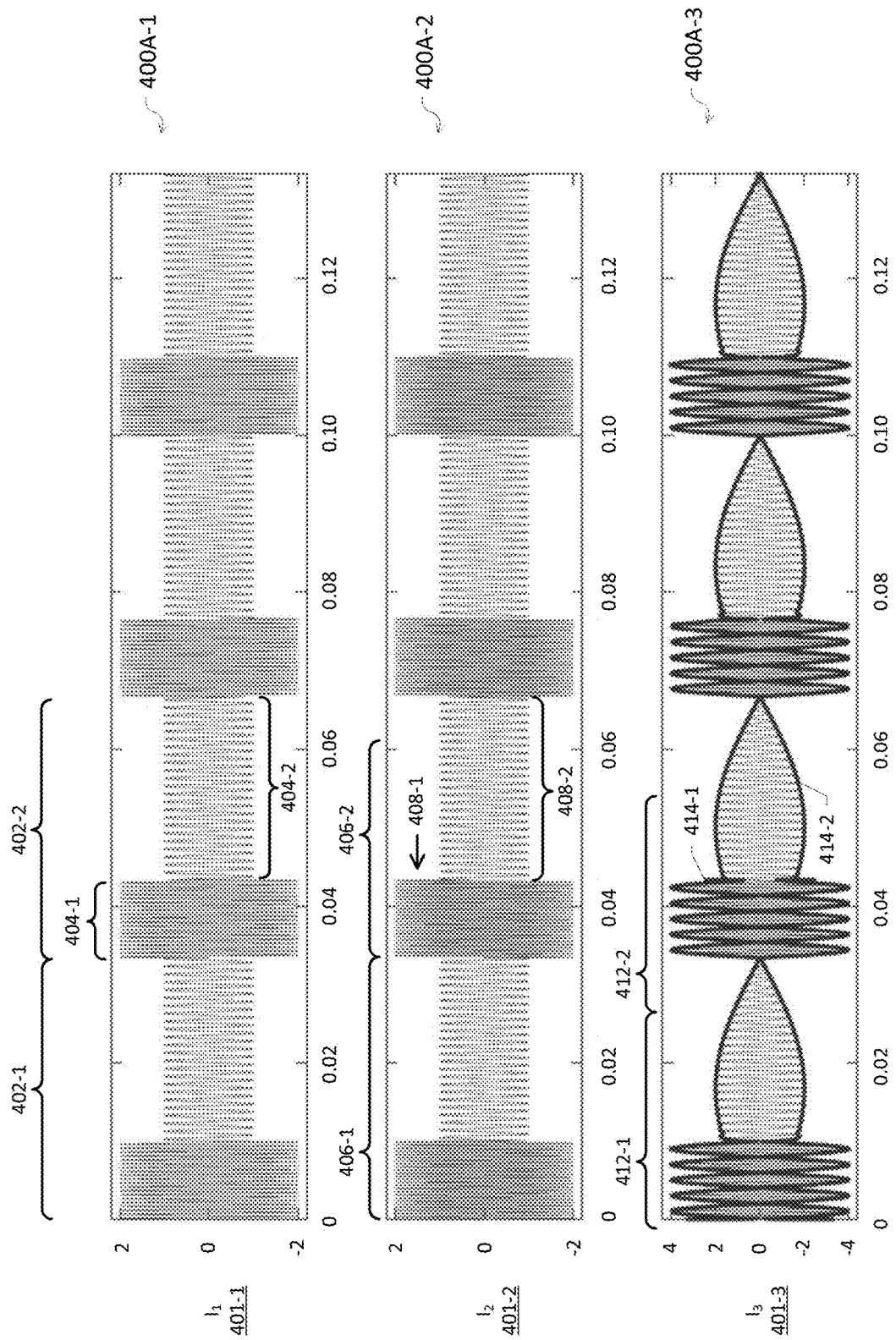
FIGS. 4A and 4B depict a panel of example input waveforms and resultant interference waveform for application in a T/STI-based therapy system according to further embodiments of the present patent disclosure.
Figure 4B:
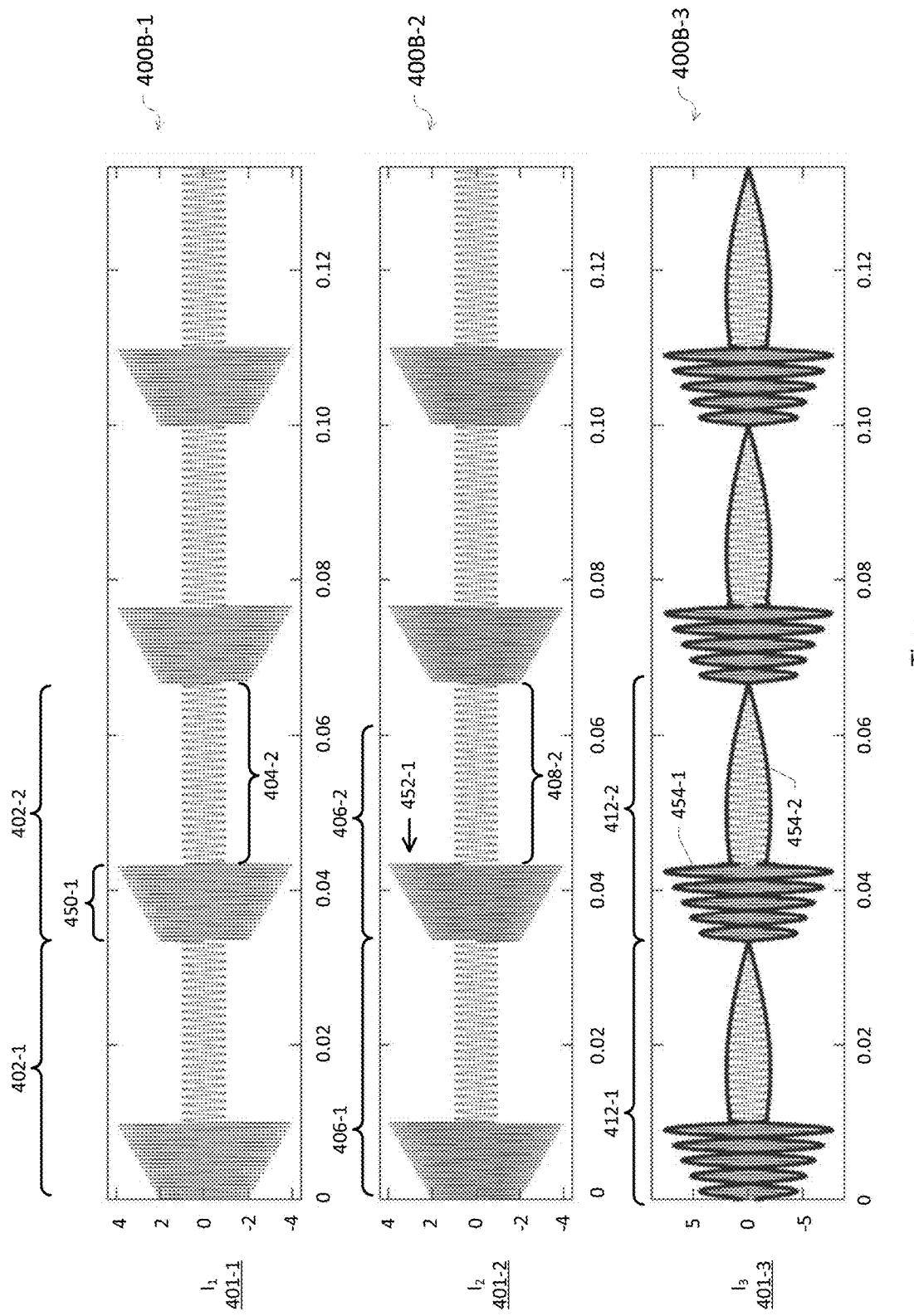

FIGS. 4A and 4B each depict a panel of example input source waveforms and resulting interference waveform for application in a CFS-based therapy system wherein more complex input waveforms are generated and applied, thereby resulting in correspondingly complex interference patterns according to some example embodiments of the present patent disclosure. In one arrangement, rather than having fixed, or unvarying, frequencies of $f_1$ and $f_2$ for input signals, a temporal dynamics may be introduced into each or either input signal applied to the corresponding electrode pair. For example, the frequency of a first input waveform may be varied periodically (with periodicity of $P_1$) to include a plurality of repeating patterns spanning over a therapy period such that each repeating pattern includes a first portion of a high frequency followed by a second portion of a low frequency (e.g., based on a first duty cycle). Likewise, the frequency of a second input waveform may also be varied periodically (with periodicity of $P_2$) to include a corresponding plurality of repeating patterns spanning over the therapy period such that each repeating pattern of the second input waveform also includes a first portion of a high frequency followed by a second portion of a low frequency (e.g., having a second duty cycle). Skilled artisans will recognize that the periodicities $P_1$ and $P_2$ as well as respective high frequency and low frequency portions of the input waveforms' repeating patterns may be related in a mathematical manner such that they can be appropriately adjusted (i.e., "tuned") to cause an interferential field exhibiting the beat phenomenon. For example, a first input source waveform $I_1$ 401-1 shown in panel 400A-1 may be provided with a plurality of repeating patterns 402-1, 402-2 wherein each repeating pattern comprises a shorter 10 ms portion of 2000 Hz at 2 mA (e.g., high frequency portion 404-1) followed by a longer 233 ms of 1000 Hz at 1 mA (e.g., low frequency portion 404-2), thereby exhibiting a first temporal or duty cycle dynamics. In similar fashion, a second input source waveform $I_2$ 401-2 shown in panel 400A-2 may be provided with a corresponding plurality of repeating patterns 406-1, 406-2 wherein each repeating pattern comprises a shorter 10 ms portion of 2500 Hz at 2 mA (e.g., high frequency portion 408-1) followed by a longer 233 ms of 1030 Hz at 1 mA (e.g., low frequency portion 408-2), thereby exhibiting a second temporal or duty cycle dynamics. A resulting interference signal 401-3 shown in panel 400A-3 is exemplified with a complex waveform having a corresponding plurality of repeating beat patterns 412-1, 412-2, each comprising a shorter high frequency portion 414-1 (e.g., a 10 ms portion of 500 Hz, which is the difference between the respective high frequencies for the shorter times of the input signals' repeating patterns) and a longer low frequency portion 414-2 (e.g., a 233 ms portion of 30 Hz, which is the difference between the respective low frequencies for the longer times of the input signals' repeating patterns). It will be further noted that the high frequency portion 414-1 comprises five spikes at 500 Hz and 4 mA (twice the amplitude of the respective high frequency portions 404-1, 408-1 of $I_1$ 401-1 and $I_2$ 401-2, whereas the low frequency portion 414-2 is devoid of any spikes.

A further variation may involve amplitude dynamics in combination with the temporal frequency dynamics described above, wherein the amplitudes of the respective high frequency portions of the input signals may be varied relative to the amplitudes of the respective low frequency portions. Taking the above example arrangement, if the first portion of 10 ms (i.e., the shorter portion) has an amplitude dynamics therein, e.g., a linear growth from 2 mA to 4 mA, in either or both input waveforms, then the resulting high frequency portion of the TTI signal would also exhibit a variable amplitude in its spikes, which have a higher amplitude than the low frequency portion of the T/STI signal, as exemplified in panels 400B-1 to 400B-3 of FIG. 4B. As illustrated, high frequency portions 450-1, 450-2 of $I_1$ 401-1 and $I_2$ 401-2, respectively, show a linear amplitude growth for 10 ms each, followed by respective low frequency portions 404-2, 408-2. Resulting waveform 401-3 has a repeating beat pattern wherein a high frequency portion 454-1 comprises five spikes that also exhibit a corresponding linear amplitude growth, e.g., from 4 mA to 8 mA, followed by the corresponding low frequency portion 454-2 at 30 Hz and 2 mA having no spikes. As noted previously, the beat pattern may be repeated over the course of a therapy period. Skilled artisans will recognize such a T/STI pattern is operative to stimulate the target tissue in a burst-like manner with a particular duty cycle, wherein the shorter high frequency portions having larger amplitudes comprise burst or "spiky" portions and the longer low frequency portions having smaller amplitudes comprise non-burst or inter-burst portions. It will be apparent upon reference hereto that various complex T/STI patterns may be generated by suitably varying the frequency and/or amplitude characteristics of the input waveforms so as to effectuate stimulation patterns having super-threshold effects (such as, e.g., tonic stimulation) and sub-threshold effects (such as, e.g., burst stimulation) in a therapy application similar to the effects achieved in some therapy applications based on implantable pulse generators described in, e.g., U.S. Pat. No. 9,656,077, entitled "COMBINATION OF TONIC AND BURST STIMULATIONS TO TREAT NEUROLOGICAL DISORDERS", incorporated by reference herein.

It will be appreciated that in one arrangement involving two or more independent current sources, an embodiment of the present patent disclosure may be configured to include appropriate control communications between the sources so as to facilitate phase locking or synchronization of the carrier stimulation waveforms. The operative principle of T/STI is that the amplitude increases when the two independent current sources are in phase and decreases when they are out of phase. When a burst starts, an example embodiment may therefore be configured such that the phase between the sources is reset and locked either with wired communication or wireless communication between the stimulators to obtain maximum benefit of T/STI.

Figure 5A:
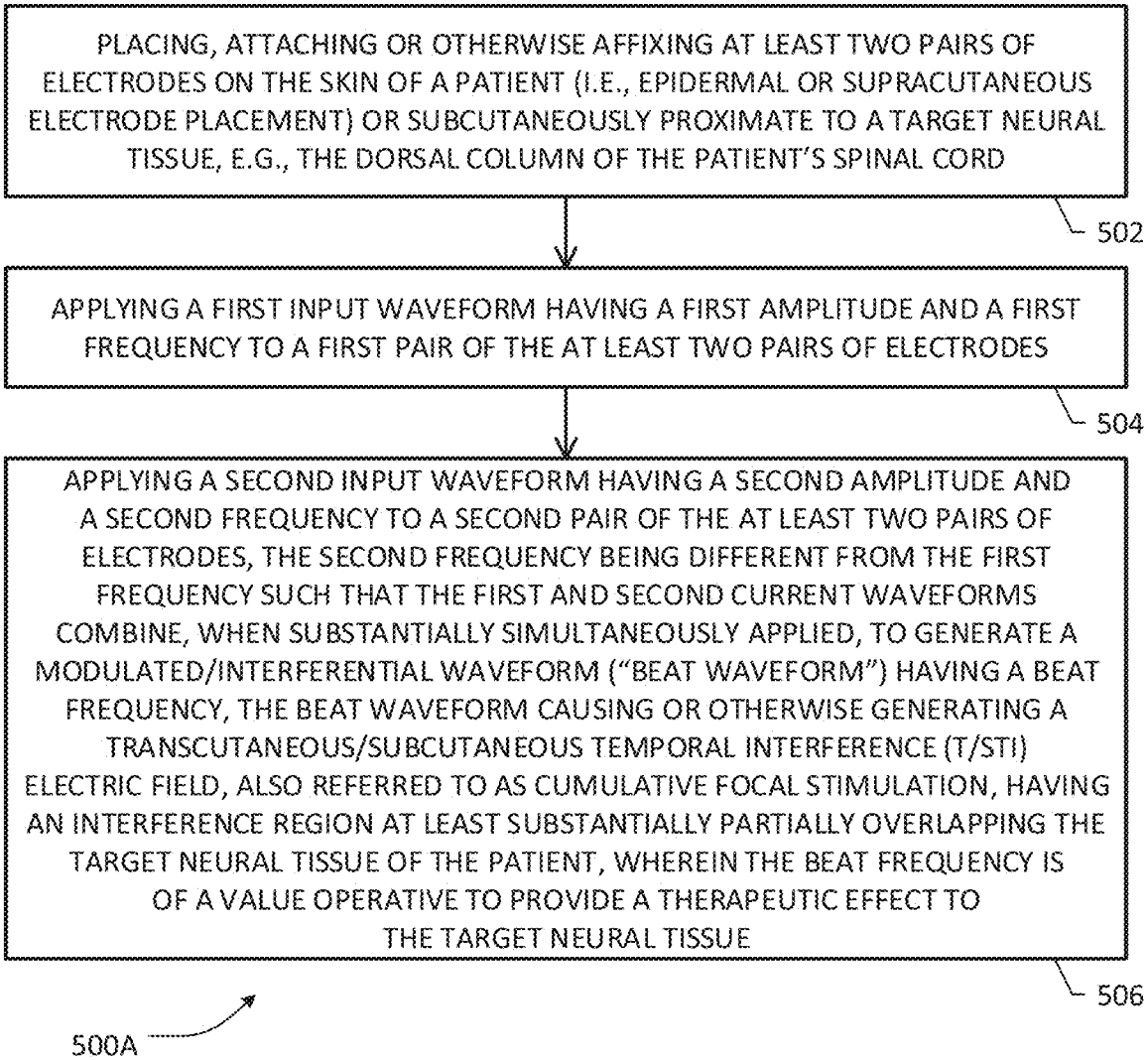

FIGS. 5A-5E depict various flowcharts illustrative of blocks, steps and/or acts that may be (re)combined in one or more arrangements with or without additional flowcharts of the present patent disclosure for facilitating CFS-based NIMI neuromodulation according to some embodiments of the present patent disclosure. Process 500A shown in FIG. 5A is exemplary of a method for providing NIMI stimulation therapy to a target neural tissue of a patient. At block 502, process 500A may involve placing, attaching or otherwise affixing at least two pairs of electrodes on the patient's body, e.g., on the skin (i.e., epidermal or supracutaneous electrode placement) or disposed minimally invasively, e.g., in a subcutaneous placement, proximate to a target neural tissue, e.g., the dorsal column of the patient's spinal cord. At block 504, a first input waveform (e.g., a first current signal) having a first amplitude and a first frequency may be applied to a first pair of the at least two pairs of electrodes. At block 506, a second input waveform (e.g., a second current signal) having a second amplitude and a second frequency may be applied to a second pair of the at least two pairs of electrodes. In one arrangement, the second frequency may be configured to be different from the first frequency such that the first and second current waveforms combine, when substantially simultaneously applied, to generate a modulated/interferential waveform (also synonymously and interchangeably referred to as a beat waveform) having a beat frequency, the beat waveform causing or otherwise generating a T/STI electric field (also referred as cumulative focal stimulation or CFS as noted previously) having an interference region at least substantially partially overlapping the target neural tissue of the patient. As described previously, the input waveforms may be configured or otherwise calibrated so that the resulting T/STI beat frequency is of a value operative to provide a therapeutic effect to the target neural tissue.

In some embodiments, the number of electrode pairs (i.e., input field sources) to be used and/or the placement of electrodes on a patient's body may depend on and/or may be calibrated based on a number of factors including but not limited to, e.g., the patient's anatomy and somatotype, target tissue morphology and electrophysiology, intended therapy, the experience, expertise and knowledge of the medical professional administering the NIMI neuromodulation therapy, among others, as well as applicable stimulation settings such as amplitude ranges, frequency ranges, temporal dynamicity relating to frequency and/or amplitude settings (e.g., to obtain more complex waveforms as described above), and the like. In some embodiments, a domain knowledgebase or an expert system may be implemented wherein a T/STI pattern database containing a repository of T/STI patterns may be developed for different combinations of electrode placement configurations, number of electrode pairs, current amplitude and frequency ranges, dynamic patterns, etc., as previously described. In some embodiments, the T/STI database may be interrogated by the medical professional prior to selecting or determining the number of electrode pairs and their placement for a given set of stimulation settings and/or for a desired T/STI pattern that includes an interference region substantially corresponding to the location of the target neural tissue of the patient for the selected electrode configuration and parameters, as set forth at block 510 of process 500B shown in FIG. 5B, which may be augmented with other example processes of the present patent disclosure.

Process 500C shown in FIG. 5C is representative of additional and/or alternative variations that may be combined in an example NIMI neuromodulation scheme according to some embodiments. At block 522, the frequency of a first input waveform (e.g., a current source) applied to an electrode pair may be maintained at a first constant value over a period of time of therapy. At block 524, the frequency of a second input waveform (e.g., a current source) applied to a second electrode pair may be maintained at a second constant value over the period of time of therapy. At block 526, process 500C may involve maintaining or varying the amplitudes/frequencies of the first and second input waveforms over the therapy period to introduce temporal/duty cycle dynamics. Further, an example therapy program may comprise settings operative to effectuate therapy portions with constant frequencies and/or amplitudes interspersed with therapy portions having frequency and/or amplitude variations. As one skilled in the art will recognize, any of the foregoing acts may be combined in numerous permutations and combinations, including some configurations where one or more acts implemented as an optional variation in an example embodiment.

Processes 500D and 500E shown in FIGS. 5D and 5E, respectively, are representative of further variations with additional details involving parametric dynamics that may be combined in an example NIMI neuromodulation scheme according to some embodiments. In one arrangement, example process 500D may involve introducing frequency dynamics in one or more of input signal sources. For example, a frequency of the first input waveform (e.g., a current source) may be varied to include repeating patterns of a first portion of a first high frequency and a second portion of a first low frequency over a period of time of therapy, as set forth at block 532. Example process 500D may also involve varying a frequency of the second input waveform (e.g., a current source) to include repeating patterns of a first portion of a second high frequency and a second portion of a second low frequency over the period of time of therapy, wherein a beat waveform includes a repeating pattern of a high frequency portion and a low frequency portion for each beat period over the therapy period. In a still further variation involving amplitude dynamics, example process 500E may involve introducing dynamics in the amplitudes of one or more of input signal sources. In one arrangement, an amplitude (e.g., a first amplitude) of the first current waveform may be varied such that a first portion comprising the first high frequency has a first high amplitude and a second portion comprising the first low frequency has a first low amplitude (block 542). Example process 500E may also involve varying an amplitude (e.g., a second amplitude) of the second current waveform such that a first portion comprising the second high frequency has a second high amplitude and a second portion comprising the second low frequency has a second low amplitude, thereby causing the high frequency portion of the beat waveform to have a higher amplitude (e.g., comprising a plurality of spikes) determined as a function of the first and second high amplitudes, which correspond to or give rise to an amplitude-modulated bursty T/STI activation region (block 544).

Figure 5F:
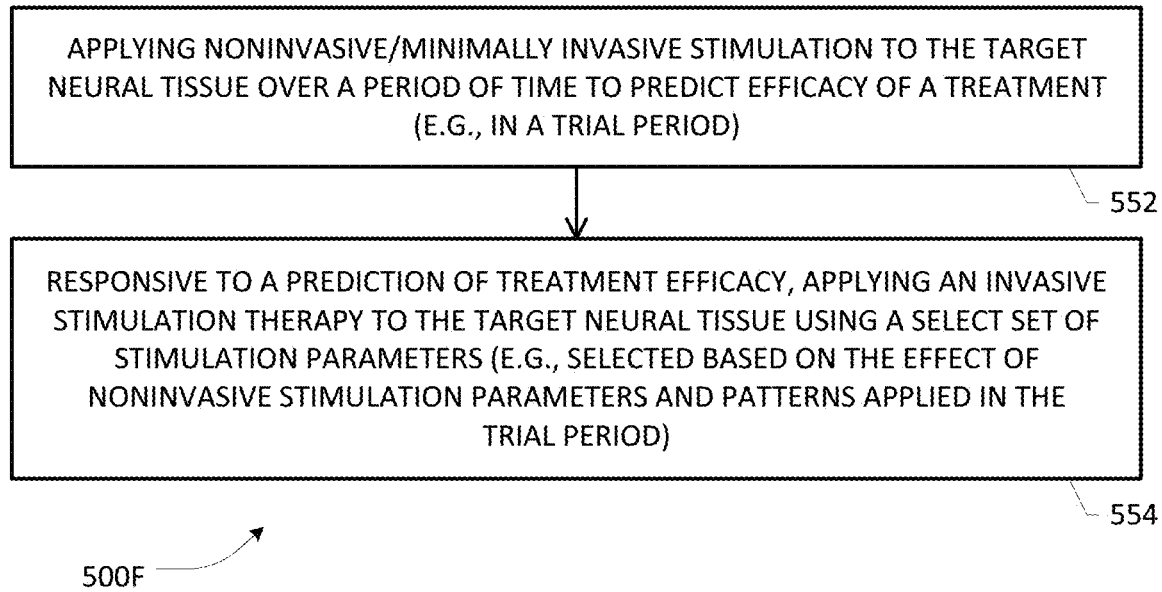

FIG. 5F depicts additional variations that may be implemented in respect of designing or planning a neuromodulation method 500F for providing therapy to a target neural tissue of a patient according to some embodiments. At block 552, example method 500F may involve applying NIMI stimulation to the target neural tissue over a period of time to predict efficacy of a treatment. In one arrangement, the NIMI stimulation is provided by generating a beat waveform having a beat frequency due to interference of two or more input source waveforms as described in detail hereinabove, wherein the beat waveform is operative to cause a T/STI electric field having an interference region at least partially overlapping the target neural tissue of the patient. Appropriate waveform engineering techniques may be applied such that the beat frequencies of the beat waveforms are operative to impart a therapeutic effect to the target neural tissue. At block 554, responsive to a prediction and/or observation of treatment efficacy, an invasive stimulation therapy may be applied to the target neural tissue using a select set of stimulation parameters, wherein appropriate number of implantable electrodes, electrode types and/or stimulation settings may be selected based on the results of the NIMI stimulation trial period, including applicable burst stimulation parameters if so indicated.

Figure 6:
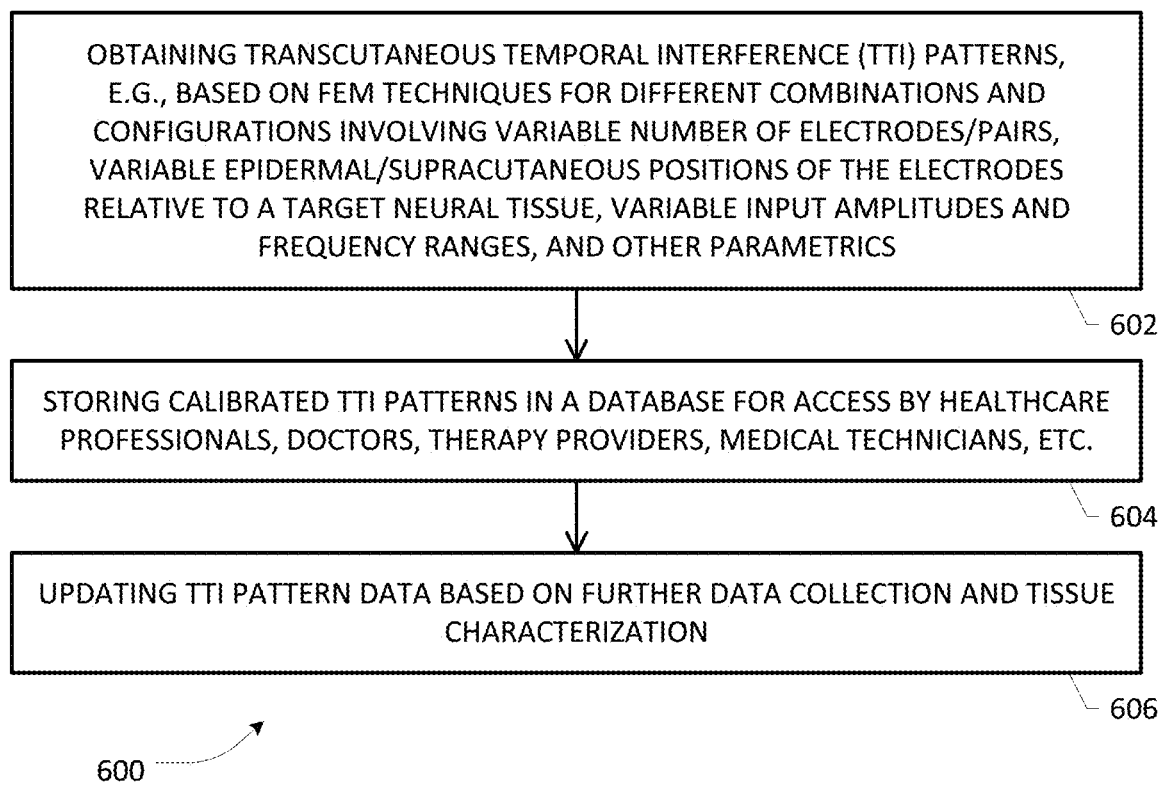
FIG. 6 depicts a flowchart illustrative of blocks, steps and/or acts that may be (re)combined in one or more arrangements with or without additional flowcharts of the present patent disclosure for purposes of some embodiments of the present patent disclosure.

FIG. 6 depicts a flowchart illustrative of blocks, steps and/or acts that may be (re)combined in one or more arrangements with or without additional flowcharts of the present patent disclosure for purposes of a T/STI-based NIMI neuromodulation method according to a further embodiment of the present patent disclosure. Example process 600 may involve obtaining T/STI patterns for different combinations and configurations involving variable number of electrodes/pairs, variable epidermal, supracutaneous, subcutaneous, or minimally invasive positions of the electrodes relative to a target neural tissue, variable input waveform amplitudes and frequency ranges, and other parametrics, as previously noted. In one arrangement, suitable computational modeling techniques (e.g., finite element modeling (FEM)) may be employed in conjunction with one or more animal models or one or more human models to predict the propagation and envelope location of electric fields in a subject. Machine learning (ML) techniques may also be used, e.g., based on field data, clinical studies, etc., in combination with computational modeling techniques to obtain more precise estimates of electric field propagation and CFS interference region prediction for different configurations and calibrations. The foregoing features are cumulatively set forth at block 602. At block 604, calibrated T/STI patterns may be stored in a database, e.g., on a network and/or downloadable to a local device, for access by healthcare professionals, doctors, therapy providers, medical technicians, patients, etc. (block 604). At block 606, the T/STI pattern database may be updated based on further data collection, target tissue characterization, control inputs responsive to supervised training by human/automata experts, and the like.

Figure 7:
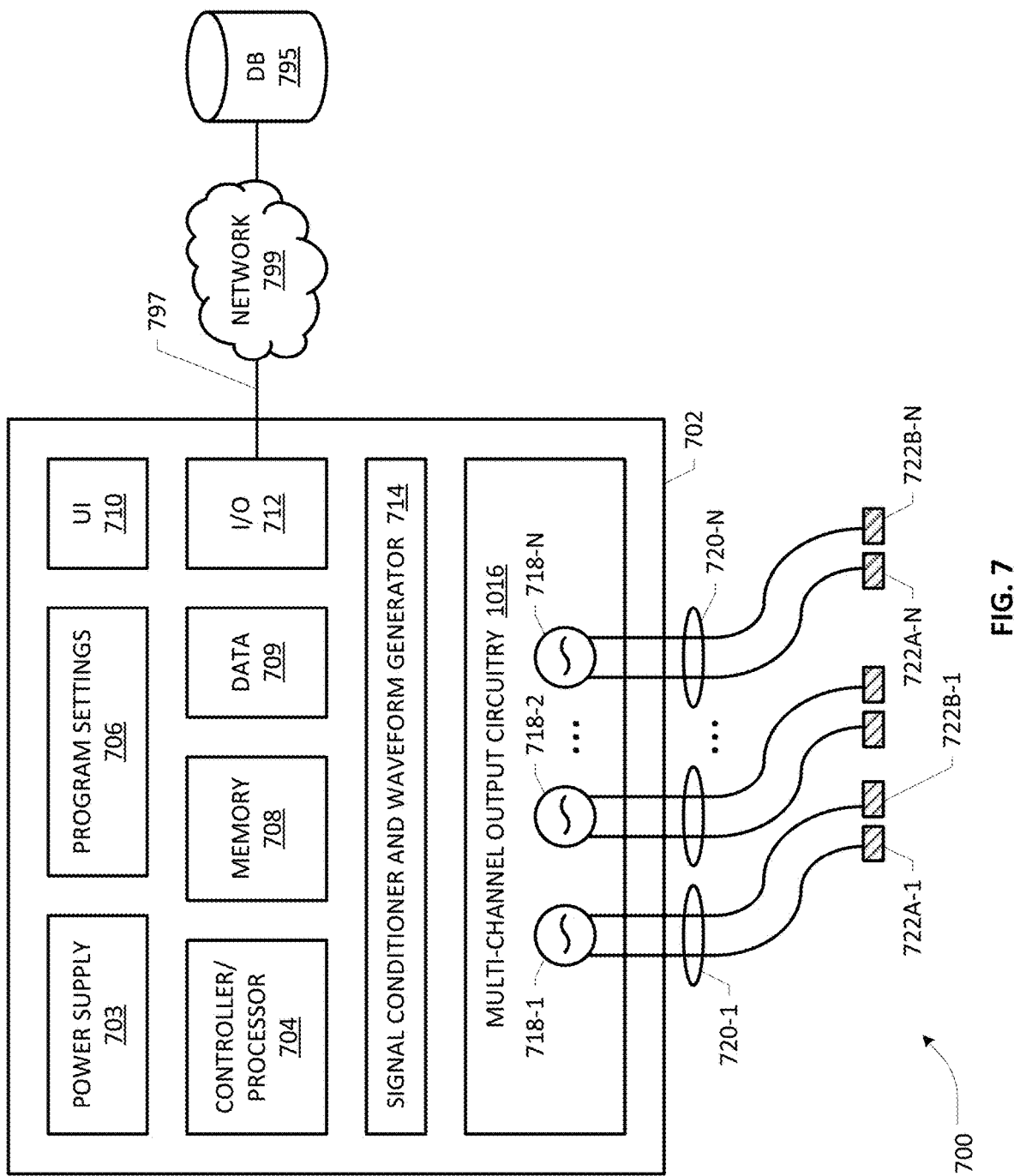
FIG. 7 is a block diagram of a NIMI neuromodulation apparatus according to an example embodiment of the present patent disclosure.

FIG. 7 is a block diagram of a noninvasive/minimally invasive (NIMI) neuromodulation apparatus or device 700 according to an example embodiment of the present patent disclosure. Apparatus 700 may comprise commercial off-the-shelf (COTS) equipment such as a portable computer, smartphone, tablet, phablet, laptop, or the like, or a proprietary portable medical/healthcare device, which may be configured to execute a therapy application program or "app", wherein multiple modules or blocks may be provided relating to control, therapy/diagnostics, and/or input source generation and waveform engineering for facilitating NIMI neuromodulation according to the teachings herein. A controller/processor 704 may be configured to execute program instructions stored in one or more persistent memory modules 708 in association with program settings 706 and other modules to generate appropriate oscillating electrical signals (e.g., current signals) having suitable amplitudes and frequencies according to known or heretofore unknown signal/function generation and conditioning techniques. One or more user interfaces (UI) 710 may be provided to facilitate the patient and/or the medical technician (or their respective agents) to interact with the various modules of apparatus 700 to activate a therapy application or program, typically based on one or more stored program settings 706. Such UI(s) 710 may comprise touch screens, display devices, touch pads, keypads, pointing devices, audio/video interfaces, etc. Signal conditioning and waveform/function generator circuitry 714 may comprise a variety of active and passive electronic components, e.g., integrated circuits (ICs), phase-locked loops (PLLs), mixed-signal circuitry, analog circuitry, digital circuitry, etc., configured to generate oscillating signals comprising sinusoids as well as non-sinusoids in some embodiments. An output driver circuit 716 may be operative as multi-channel patient interface circuitry for facilitating independent selection of a plurality of channels, each driven by a corresponding waveform source 718-1 to 718-N, respectively, operating in association with signal conditioning circuitry 714, that can generate signals having frequencies in a range of a few hundred Hz to a few thousand Hz and amplitudes ranging from fractions of a milliamp to one or more Amps. Each source 718-1 to 718-N may be coupled to respective electrode pairs 722A-1/722B-1 to 722A-N/722B-N wirelessly or via wires or leads, as exemplified by channel paths 720-1 to 720-N. In some particular embodiments, the various circuit modules herein may be configured to generate input signals having properties such that the resultant interference waveforms are similar or identical to the waveforms exemplified hereinabove, e.g., described with respect to FIGS. 3 and FIGS. 4A-4B, without limitation. Depending on implementation and therapy application, electrode pairs 722A-1/722B-1 to 722A-N/722B-N may comprise conductive gel pad electrodes, sponge electrodes, patch electrodes, etc., having adhesive surfaces in different sizes and/or shapes. In some additional or alternative embodiments, one or more electrode pairs 722A-1/722B-1 may comprise subcutaneous electrode pairs, wherein either or both types of temporal interference may be effectuated to generate suitable beat waveforms. In still further variations, a cuff electrode arrangement may also be provided additionally or alternatively. One or more input/output (I/O) modules 712 are operative to effectuate inter-device and/or network communications, e.g., via wireless and/or wired communication interfaces or paths 797 configured to interoperate with suitable internal (e.g., on-site) and/or external (off-site) data communication infrastructure(s) 799, which may include other medical devices, implantable/external pulse generators, patient controllers, clinician programmers, remote therapy management servers, mobile device management (MDM) systems, medical datacenters, etc. In one arrangement, apparatus 702 may be configured to access network entities, e.g., database(s) 795 for obtaining TTI/CFS pattern data and/or calibration data for different electrode configurations and stimulation settings. Additionally, alternatively and/or optionally, a local database 709 may be provided as part of apparatus 700 for facilitating local look-up and retrieval of such data, which may be periodically updated based on the network database 795. A suitable power supply 703 (e.g., a rechargeable supply) may be provided for powering the various modules of apparatus 700, which may be augmented with an external line power interface in some embodiments.

Based on the foregoing, skilled artisans will recognize that example embodiments may be advantageously used in various noninvasive therapy applications such as SCS and DRG stimulation for chronic pain relief, thereby potentially eliminating or reducing the need for more traumatic surgical procedures required for implanting and/or explanting invasive neurostimulator devices such as IPGs. Further, some embodiments may be configured to generate suitable "priming" pulses used in gait training (e.g., after a stroke), as well as in the treatment of certain motor/neurological disorders, e.g., Parkinson's disease, disorders such as shaking and tremors, slowed movement or bradykinesia, and other gait-related dysfunctions. Some embodiments may be configured to facilitate motor rehabilitation, e.g., either by activating the alpha motor neurons in the ventral horn of the spinal cord or by activating the sensory fibers and inducing reflexes. In some additional and/or alternative arrangements, a NIMI neuromodulator may be deployed in conjunction with a traditional invasive IPG device (e.g., for SCS and DRG therapy) wherein the implanted electrodes and the external electrodes may be energized simultaneously in order to "tune" an interference zone in a highly granular manner for more precise localization of stimulation/therapy energy. An additional benefit of the present patent disclosure is where an embodiment herein may be deployed initially to verify and/or predict if stimulation treatment is efficacious for a patient, and if so, enabling an informed decision to proceed with a traditional invasive (and more permanent) IPG option. Still further, some embodiments may be particularly configured for treating disorders such as urinary and fecal dysfunctions, sexual dysfunctions, e.g., either by targeting the spinal cord or spinal nerves associated with select vertebral segments. For example, it is known that by stimulating spinal nervous tissue associated with certain specific vertebral segments, e.g., tissue associated with at least one of the $4^{th}$ through $9^{th}$ thoracic vertebral segments, a wide variety of eating and/or gastrointestinal disorders and/or conditions such as heartburn, bloating, postoperative ileus, abdominal pain and discomfort, early satiety, abdominal pain, epigastric pain, nausea, vomiting, burbulence, regurgitation, intestinal pseudo-obstruction, anal incontinence, gastroesophageal reflux disease, irritable bowel syndrome, dyspepsia, chronic constipation, gastroparesis, ulcerative colitis, pancreatitis, Crohn's disease, menstrual cramps, spastic and interstitial cystitis and ulcers, obesity, anorexia nervosa, and bulimia nervosa, may be treated. Additional details relating to the application of SCS for the treatment of gastrointestinal disorders may be found in, e.g., U.S. Pat. No. 8,214,047, entitled "METHOD OF USING SPINAL CORD STIMULATION TO TREAT GASTROINTESTINAL AND/OR EATING DISORDERS OR CONDITIONS", incorporated by reference herein, wherein an embodiment of the present patent disclosure may be deployed in lieu of or in association with an invasive SCS treatment modality.

It will therefore be appreciated that some of the terms used in connection with one or more embodiments herein may have broader meaning depending on the therapy being contemplated. Without limitation, a summary of the terms relevant for purposes of some embodiments is set forth below.

As used herein, the term "modulate" may refer to the ability to regulate positively or negatively neuronal activity, including but not limited to, neuronal activity via stimulation of the spinal cord or spinal nervous tissue associated with various vertebral segments which innervates several regions of a patient's body. Further, the term modulate can be used to refer to an increase, decrease, masking, altering, overriding or restoring neuronal activity, including but not limited to, neuronal activity associated with various nerve roots. Modulation of neuronal activity, such as that associated with the thoracic nerve roots, for example, can affect pain and/or gastric activity or gastric motility of a subject, abdominal pain, intestinal motility, esophageal motility, among other effects, for purposes of some embodiments.

As used herein, the term "neuronal" may refer to, without limitation, a neuron which is a morphologic and functional unit of the brain, spinal column, and peripheral nerves for purposes of some embodiments.

As used herein, the term "stimulate" or "stimulation" may refer to electrical and/or electrically-induced chemical modulation of selected cervical, thoracic or lumbar nervous tissue, associated nerve roots, segments, or areas of the spinal cord associated with respective vertebral segment(s) for purposes of some embodiments.

The phrase "spinal cord stimulation" as used herein may include, without limitation, stimulation of any spinal nervous tissue, including spinal neurons, accessory neuronal cells, nerves, nerve roots, nerve fibers, or tissues, that are associated with the spinal cord. It is contemplated that spinal cord stimulation may comprise stimulation of one or more areas associated with one or more vertebral segments for purposes of some embodiments.

As used herein, "spinal nervous tissue" may refer to, without limitation, nerves, neurons, neuroglial cells, glial cells, neuronal accessory cells, nerve roots, nerve fibers, nerve rootlets, parts of nerves, nerve bundles, mixed nerves, sensory fibers, motor fibers, dorsal root, ventral root, dorsal root ganglion, spinal ganglion, ventral motor root, general somatic afferent fibers, general visceral afferent fibers, general somatic efferent fibers, general visceral efferent fibers, grey matter, white matter, the dorsal column, the lateral column, and/or the ventral column associated with the spinal cord for purposes of some embodiments.

As used herein, "spinal nervous tissue associated with a vertebral segment" may refer to nervous tissue associated any or a combination of cervical, thoracic, lumbar, and/or sacral vertebral segments.

As used herein, the terms "therapeutic effect" and/or "treatment" may refer to stimulating certain nervous tissue of the spinal cord so that the subject has an improvement in the pain condition and/or disease, for example, observed as beneficial or desired clinical results. For purposes of some embodiments of the present patent disclosure, beneficial or desired clinical results may include, but are not limited to, alleviation of symptoms, alleviation of pain, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or non-volatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Also, some blocks in the flowcharts may be optionally omitted. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Where the phrases such as "at least one of A and B" or phrases of similar import are recited, such a phrase should be understood to mean "only A, only B, or both A and B." Reference to an element in the singular is not intended to mean "one and only one" unless explicitly so stated, but rather "one or more." Moreover, the terms "first," "second," and "third," etc. employed in reference to elements or features are used merely as labels, and are not intended to impose numerical requirements, sequential ordering or relative degree of significance or importance on their objects. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A method for providing therapy to a target neural tissue of a patient, the method comprising:
   determining placement of at least two pairs of electrodes based on interrogating a temporal interference (TI) pattern database having a plurality of TI patterns for different combinations of electrode placement configurations, number of electrode pairs, a range of amplitudes corresponding respectively to a first input waveform and a second input waveform, and a range of frequencies corresponding respectively to the first input waveform and the second input waveform;
   affixing at least two pairs of electrodes noninvasively on a body of the patient at respective locations relative to the target neural tissue based on the placement of the at least two pairs of electrodes determined by interrogating the TI pattern database;
   applying a first particular input waveform having a first amplitude and a first frequency to a first pair of the at least two pairs of electrodes; and
   applying a second particular input waveform having a second amplitude and a second frequency to a second pair of the at least two pairs of electrodes, the second frequency configured to be different from the first frequency such that the first and second input waveforms combine, when substantially simultaneously applied, to generate a beat waveform having a beat frequency due to interference, the beat waveform causing a TI electric field having an interference region at least partially overlapping the target neural tissue of the patient, wherein the beat frequency is of a value operative to impart a therapeutic effect to the target neural tissue.

2. The method as recited in claim 1, further comprising:
   maintaining the first frequency of the first input waveform at a first constant value over a therapy period; and
   maintaining the second frequency of the second input waveform at a second constant value over the therapy period.

3. The method as recited in claim 1, further comprising:
   varying the first frequency of the first input waveform to include repeating patterns of a first portion of a first high frequency and a second portion of a first low frequency over a therapy period; and
   varying the second frequency of the second input waveform to include repeating patterns of a first portion of a second high frequency and a second portion of a second low frequency over the therapy period, wherein the beat waveform includes a corresponding repeating pattern of a high frequency portion and a low frequency portion for each beat period over the therapy period.

4. The method as recited in claim 3, further comprising:
   varying the first amplitude of the first input waveform such that the first portion comprising the first high frequency has a first high amplitude and the second portion comprising the first low frequency has a first low amplitude; and
   varying the second amplitude of the second input waveform such that the first portion comprising the second high frequency has a second high amplitude and the second portion comprising the second low frequency has a second low amplitude, thereby causing the high frequency portion of the beat waveform to have a higher amplitude determined as a function of the first and second high amplitudes.

5. The method as recited in claim 4, wherein the first high amplitude of the first input waveform and the second high amplitude of the second input waveform are substantially identical.

6. The method as recited in claim 4, wherein the first low amplitude of the first input waveform and the second low amplitude of the second input waveform are substantially identical.

7. A neuromodulator for providing therapy to a target neural tissue of a patient, the neuromodulator comprising:
   a first input source operative to generate a first input waveform;
   a second input source operative to generate a second input waveform;
   a first and a second pair of electrodes attachable at respective locations relative to the target neural tissue of the patient, wherein the respective locations are determined based on interrogating a temporal interference (TI) pattern database having a plurality of TI patterns for different combinations of electrode placement configurations, number of electrode pairs, a range of amplitudes corresponding respectively to a first input waveform and a second input waveform, and a range of frequencies corresponding respectively to the first input waveform and the second input waveform; and
   a controller configured to control the first and second input sources for:
      applying the first input waveform to the first pair of the electrodes, the first input waveform having a first amplitude and a first frequency; and
      applying the second input waveform to the second pair of the electrodes, the second input waveform having a second amplitude and a second frequency, wherein the second frequency is configured to be different from the first frequency such that the first and second input waveforms combine, when substantially simultaneously applied, to generate a beat waveform having a beat frequency due to interference, the beat waveform causing a temporal interference (TI) electric field having an interference region at least partially overlapping the target neural tissue of the patient, wherein the beat frequency is of a value operative to impart a therapeutic effect to the target neural tissue.

8. The neuromodulator as recited in claim 7, wherein the controller is further configured to perform:
   maintaining the first frequency of the first input waveform at a first constant value over a therapy period; and
   maintaining the second frequency of the second input waveform at a second constant value over the therapy period.

9. The neuromodulator as recited in claim 7, wherein the controller is further configured to perform:
   varying the first frequency of the first input waveform to include repeating patterns of a first portion of a first high frequency and a second portion of a first low frequency over a therapy period; and
   varying the second frequency of the second input waveform to include repeating patterns of a first portion of a second high frequency and a second portion of a second low frequency over the therapy period, wherein the beat waveform includes a corresponding repeating pattern of a high frequency portion and a low frequency portion for each beat period over the therapy period.

10. The neuromodulator as recited in claim 9, wherein the controller is further configured to perform:

varying the first amplitude of the first input waveform such that the first portion comprising the first high frequency has a first high amplitude and the second portion comprising the first low frequency has a first low amplitude; and varying the second amplitude of the second input waveform such that the first portion comprising the second high frequency has a second high amplitude and the second portion comprising the second low frequency has a second low amplitude, thereby causing the high frequency portion of the beat waveform to have a higher amplitude determined as a function of the first and second high amplitudes.

11. The neuromodulator as recited in claim 10, wherein the first high amplitude of the first input waveform and the second high amplitude of the second input waveform are substantially identical.

12. The neuromodulator as recited in claim 10, wherein the first low amplitude of the first input waveform and the second low amplitude of the second input waveform are substantially identical.

13. A system comprising:
a memory storing a temporal interference (TI) pattern database having a plurality of TI patterns for different combinations of electrode placement configurations, number of electrode pairs, a range of amplitudes corresponding respectively to a first input waveform and a second input waveform, and a range of frequencies corresponding respectively to the first input waveform and the second input waveform;

a neuromodulator for providing therapy to a target neural tissue of a patient by using a temporal interference (TI) pattern operative to be caused by at least two input sources comprising a first input source operative to generate a first input waveform having a first amplitude and a first frequency and a second input source operative to generate a second input waveform having a second amplitude and a second frequency; and at least two pairs of patch electrodes attachable proximate to the target neural tissue of the patient, the at least two pairs of patch electrodes coupled to respective input sources via corresponding leads, and wherein placement of at least two pairs of patch electrodes is determined based on interrogating a temporal interference (TI) pattern database;

wherein the neuromodulator includes a controller configured to control the first and second input sources to generate and apply the first and second input waveforms to the respective pairs of patch electrodes such that the first and second input waveforms combine, when substantially simultaneously applied, to generate a beat waveform having a beat frequency due to interference, the beat waveform causing a TI electric field having an interference region at least partially overlapping the target neural tissue of the patient, wherein the beat frequency is of a value operative to impart a therapeutic effect to the target neural tissue.

14. The system as recited in claim 13, wherein the controller is further configured to perform:
varying the first frequency of the first input waveform to include repeating patterns of a first portion of a first high frequency and a second portion of a first low frequency over a therapy period; and varying the second frequency of the second input waveform to include repeating patterns of a first portion of a second high frequency and a second portion of a second low frequency over the therapy period, wherein the beat waveform includes a corresponding repeating pattern of a high frequency portion and a low frequency portion for each beat period over the therapy period.

15. The system as recited in claim 14, wherein the controller is further configured to perform:
varying the first amplitude of the first input waveform such that the first portion comprising the first high frequency has a first high amplitude and the second portion comprising the first low frequency has a first low amplitude; and varying the second amplitude of the second input waveform such that the first portion comprising the second high frequency has a second high amplitude and the second portion comprising the second low frequency has a second low amplitude, thereby causing the high frequency portion of the beat waveform to have a higher amplitude determined as a function of the first and second high amplitudes.

16. The system as recited in claim 15, wherein the first high amplitude of the first input waveform and the second high amplitude of the second input waveform are substantially identical.

17. The system as recited in claim 15, wherein the first low amplitude of the first input waveform and the second low amplitude of the second input waveform are substantially identical.

18. A neuromodulation method for providing therapy to a target neural tissue of a patient, the method comprising:
applying noninvasive stimulation to the target neural tissue over a period of time to predict efficacy of a treatment using at least two pairs of electrodes, wherein a placement of the at least two pairs of electrodes based on interrogating a temporal interference (TI) pattern database having a plurality of TI patterns for different combinations of electrode placement configurations, number of electrode pairs, a range of amplitudes corresponding respectively to a first input waveform and a second input waveform, and a range of frequencies corresponding respectively to the first input waveform and the second input waveform; and responsive to a prediction of treatment efficacy, applying an invasive stimulation therapy to the target neural tissue using a select set of stimulation parameters.

19. The neuromodulation method as recited in claim 18, wherein the noninvasive stimulation is provided by generating a beat waveform having a beat frequency due to interference of two or more input source waveforms, the beat waveform causing a TI electric field having an interference region at least partially overlapping the target neural tissue of the patient, wherein the beat frequency is of a value operative to impart a therapeutic effect to the target neural tissue.

* * * * *

UNITED STATES PATENT AND TRADEMARK OFFICE
CERTIFICATE OF CORRECTION

| | |
|---|---|
| PATENT NO. | : 11,931,572 B1 |
| APPLICATION NO. | : 17/133985 |
| DATED | : March 19, 2024 |
| INVENTOR(S) | : Simeng Zhang et al. |

It is certified that error appears in the above-identified patent and that said Letters Patent is hereby corrected as shown below:

In the Specification

At Column 7, Line number 22, delete "source 1046" and replace with --source 104B--.
At Column 8, Line number 21, Equation 4, delete the portion of the Equation reading "$S_{+2}$" and replace with --$S_{1+2}$--.
At Column 11, Line number 63, delete "beats per second" and replace with --40 beats per second--.

Signed and Sealed this
Fifteenth Day of October, 2024

Katherine Kelly Vidal
*Director of the United States Patent and Trademark Office*